(12) United States Patent
Olson

(10) Patent No.: US 11,172,998 B2
(45) Date of Patent: *Nov. 16, 2021

(54) SUSPENSION SYSTEM FOR REMOTE CATHETER GUIDANCE

(71) Applicant: St. Jude Medical, Cardiology Division, Inc., St. Paul, MN (US)

(72) Inventor: Eric S. Olson, Maplewood, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 283 days.

This patent is subject to a terminal disclaimer.

(21) Appl. No.: 15/786,579

(22) Filed: Oct. 17, 2017

(65) Prior Publication Data
US 2018/0132951 A1    May 17, 2018

Related U.S. Application Data

(63) Continuation of application No. 14/588,543, filed on Jan. 2, 2015, now Pat. No. 9,820,819.
(Continued)

(51) Int. Cl.
*A61B 34/30* (2016.01)
*A61B 90/57* (2016.01)
(Continued)

(52) U.S. Cl.
CPC .............. *A61B 34/30* (2016.02); *A61B 90/50* (2016.02); *A61B 90/57* (2016.02); *A61B 5/6852* (2013.01);
(Continued)

(58) Field of Classification Search
CPC ......... A61B 34/30; A61B 90/50; A61B 34/37; A61B 90/57; A61B 5/6852;
(Continued)

(56) References Cited

U.S. PATENT DOCUMENTS

| 4,934,278 A | * | 6/1990 | Tanita | .................... B23Q 5/385 104/119 |
| 5,308,352 A | * | 5/1994 | Koutrouvelis | ..... A61B 17/3403 604/116 |

(Continued)

FOREIGN PATENT DOCUMENTS

WO    2012153871 A1    11/2012

OTHER PUBLICATIONS

European search report for EP Application No. 15150389, dated Jun. 10, 2015, pp. 1-3.

*Primary Examiner* — Catherine M Voorhees
(74) *Attorney, Agent, or Firm* — Dykema Gossett PLLC

(57) ABSTRACT

A robotic catheter system includes an arch-shaped suspension system comprising a first and second vertical span, a horizontal span between the pair of vertical spans, and at least one robotic catheter head coupled to the horizontal span. The arch-shaped suspension system can include a pair of linear guide blocks that can be attached to a patient bed and in some embodiments the linear guide blocks can be configured to slidably move along a rail. The arch-shaped suspension system can be moved to allow for proper placement of the arch-shaped suspension system for use on a patient or for placing the system away from a patient or for storage. In some embodiments the robotic catheter system can include a suspension system cart for storing and moving the arch-shaped suspension system.

9 Claims, 26 Drawing Sheets

Related U.S. Application Data

(60) Provisional application No. 61/925,489, filed on Jan. 9, 2014.

(51) Int. Cl.
| | | |
|---|---|---|
| *A61B 90/50* | (2016.01) | |
| *A61B 5/00* | (2006.01) | |
| *A61M 25/01* | (2006.01) | |
| *A61B 18/14* | (2006.01) | |
| *A61B 18/00* | (2006.01) | |
| *A61B 34/37* | (2016.01) | |

(52) U.S. Cl.
 CPC .......... *A61B 18/1492* (2013.01); *A61B 34/37* (2016.02); *A61B 2018/00577* (2013.01); *A61B 2018/00839* (2013.01); *A61B 2034/301* (2016.02); *A61B 2090/571* (2016.02); *A61M 25/0105* (2013.01)

(58) Field of Classification Search
 CPC .......... A61B 18/1492; A61B 2034/301; A61B 2090/571; A61B 2018/00577; A61B 2018/00839; A61B 90/10; A61B 90/11; A61M 25/0105
 See application file for complete search history.

(56) References Cited

U.S. PATENT DOCUMENTS

| | | | |
|---|---|---|---|
| 9,820,819 B2* | 11/2017 | Olson | A61B 5/6852 |
| 2008/0167750 A1* | 7/2008 | Stabler | A61B 17/12122 |
| | | | 700/245 |
| 2009/0247993 A1* | 10/2009 | Kirschenman | A61M 25/0147 |
| | | | 606/1 |
| 2011/0105954 A1* | 5/2011 | Cohen | A61M 25/0133 |
| | | | 600/585 |
| 2014/0249546 A1* | 9/2014 | Shvartsberg | B25J 18/005 |
| | | | 606/130 |

* cited by examiner

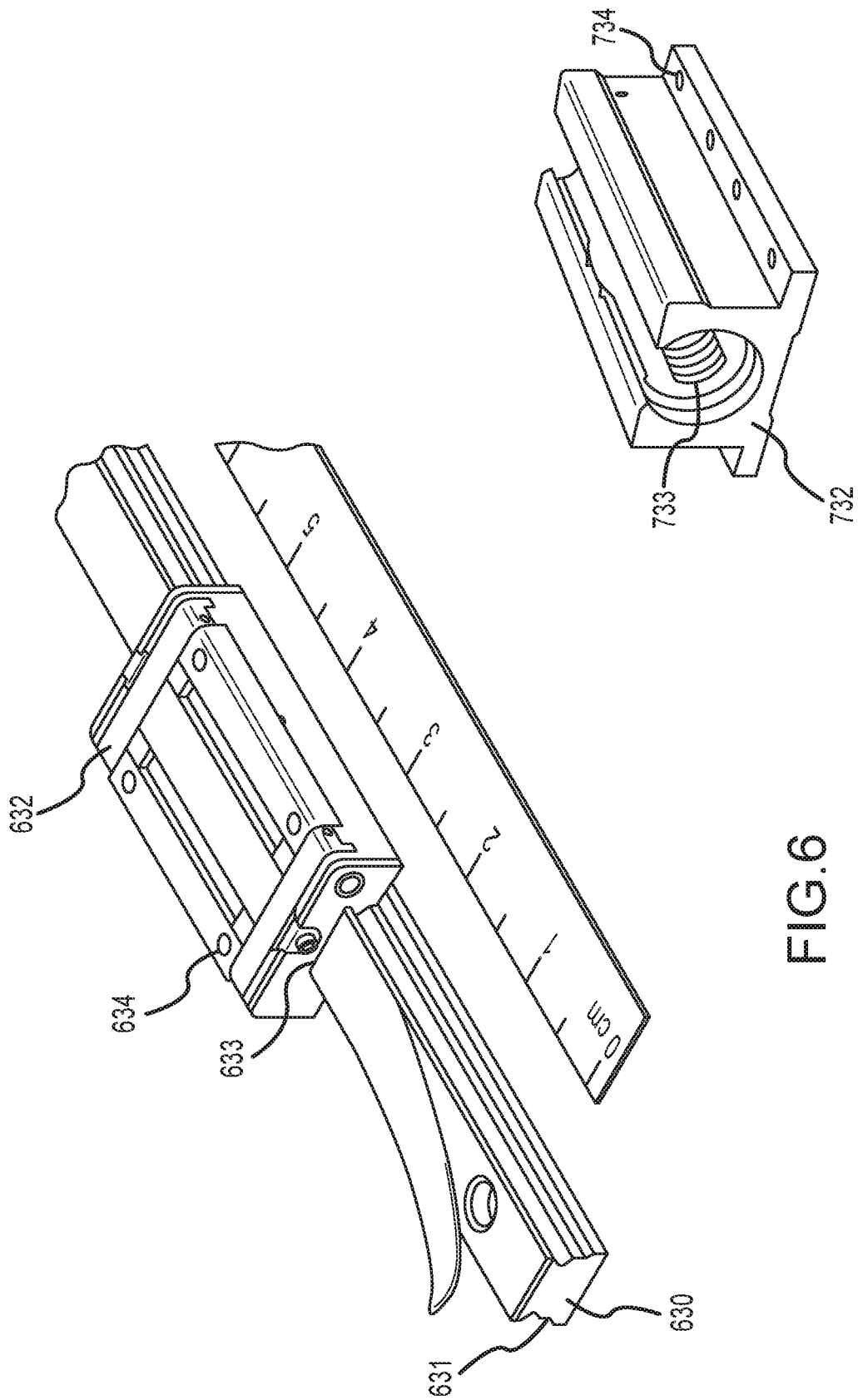

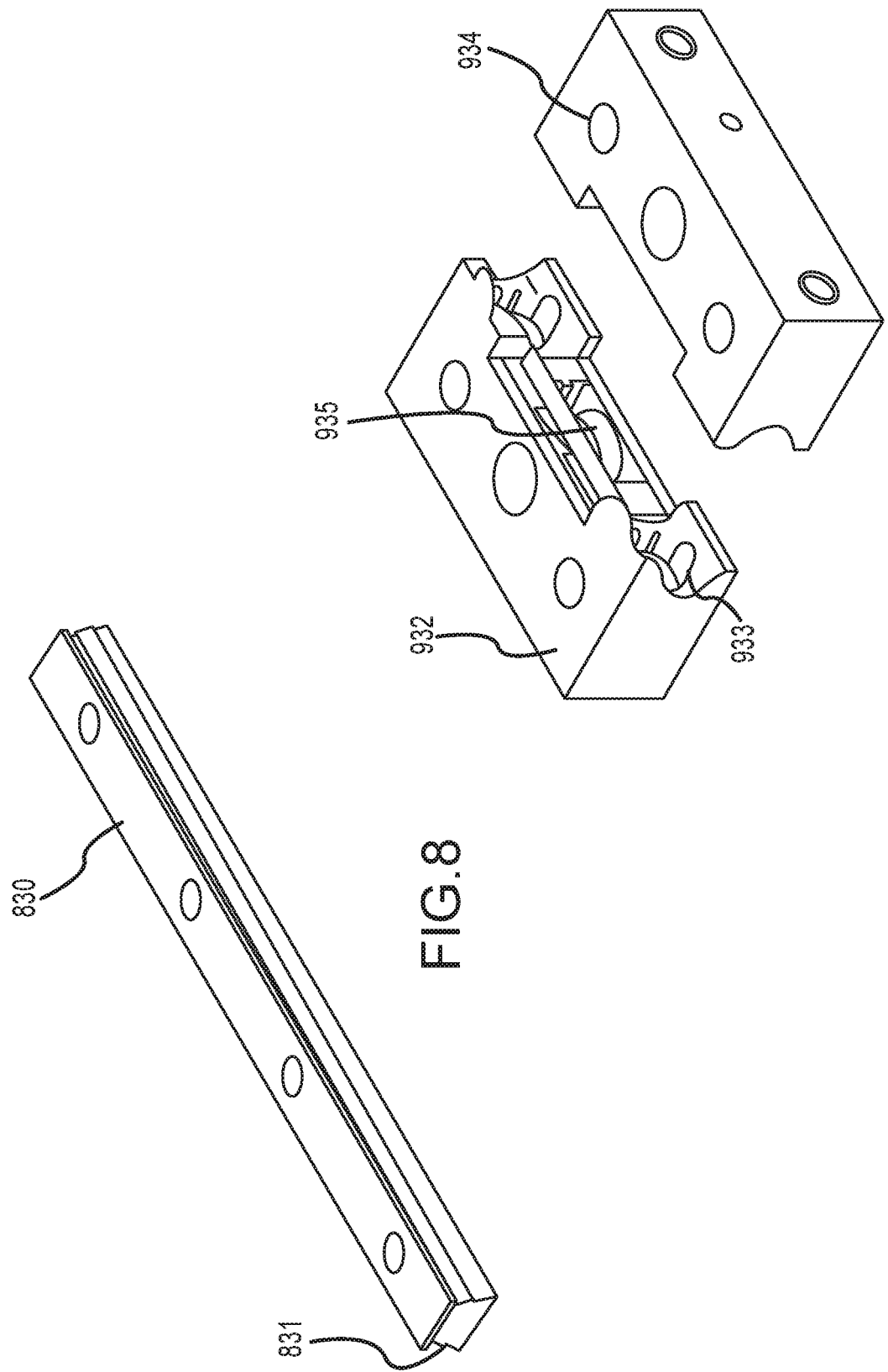

SUSPENSION SYSTEM FOR REMOTE CATHETER GUIDANCE

CROSS-REFERENCE TO RELATED APPLICATIONS

This application is a continuation of U.S. application Ser. No. 14/588,543, filed 2 Jan. 2015 (the '543 application), which claims the benefit of U.S. provisional application No. 61/925,489 (the '489 application), filed 9 Jan. 2014. The '543 application and the '489 application are both hereby incorporated by reference in their entirety as though fully set forth herein.

BACKGROUND a. Field

This disclosure relates to robotic catheter systems, apparatuses, and methods for automated control of a catheter and related components. In particular, the instant disclosure relates to a suspension system for a robotic catheter system for manipulating a catheter and related components.

b. Background

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrioventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

The inventors herein have thus recognized a need for a system and method for precise and dynamic automated control of a catheter and its related components, for example, for diagnostic, therapeutic, mapping and ablative procedures, that will minimize and/or eliminate procedural variability due to a user's skill level. The inventors herein have recognized still other shortcomings of the prior art, such as, for example, a need for a system and method for performing user-specified procedures at the patient site or from a remote location.

BRIEF SUMMARY

It is desirable to provide a system and method for precise and dynamic automated control of a catheter and its related components. In particular, it is desirable to provide a system and method for precise and dynamic automated control, for example, for diagnostic, therapeutic, mapping and ablative procedures, that will minimize and/or eliminate procedural variability due to a user's skill level, with the procedures being optionally performed at the patient site or from a remote location.

The instant disclosure, in at least one embodiment, relates to an arch-shaped suspension system comprising a first vertical span, a second vertical span, a horizontal span, and a robotic catheter head. The horizontal span can separately connect the pair of vertical spans and the robotic catheter head can be configured to operably connect or engage with the horizontal span. The first and second vertical spans can be configured to releaseably couple to a patient bed. In one embodiment, the arch-shaped suspension system can further comprise a first linear guide block coupled to the first vertical span and a second linear guide block coupled to the second vertical span. The first and second linear guide blocks can include a guide housing and at least one roller. The at least one roller can be configured for moving the suspension system along a linear guide track and the guide housing can be configured to couple to the linear guide track. In an embodiment, the robotic catheter head can further comprise a catheter cartridge and a sheath cartridge. In another embodiment the robotic catheter head is a first robotic catheter head and the arch-shaped suspension system further comprises a second robotic catheter head. In yet another embodiment, the robotic catheter head can be coupled to a robotic mount that can be operably coupled to the horizontal span. The robotic mount can be configured to be slidably movable along the horizontal span and the robotic catheter head can be configured to be slidably moveable along the robotic mount. The robotic mount can further comprise a coupler extension that can be coupled to the robotic catheter head and can be coupled to the robotic mount. The coupler extension can be configured to adjust at least one of the extension, pan, rotation, pitch, and yaw of the robotic catheter head. In another embodiment, the horizontal span can be configured to be rotated such that the robotic catheter head can be placed in a vertical position.

In another embodiment, a robotic catheter system comprises an arch-shaped suspension system including a first vertical span, a second vertical span, a horizontal span and a robotic catheter head. The robotic catheter system further comprises a suspension system cart including a cart body, a first cart rail, and a second cart rail. The horizontal span of the arch-shaped suspension system can be coupled to the first and second vertical spans. The robotic catheter head can be operably connected to the horizontal span and the first and second vertical span can be configured to releaseably couple to the suspension system cart. In one embodiment the suspension cart can be configured to be movable such that the first cart rail can be placed adjacent a first extension rail of a patient bed, and the second cart rail can be placed adjacent a second extension rail of the patient bed. The arch-shaped suspension system can be configured to slidably move from the first and second cart rails to the first and second extension rails.

In another embodiment, an arch-shaped suspension system comprises a first vertical span, a second vertical span, a horizontal span, a first coupler extension, a first robotic catheter head, a second robotic catheter head, and a third robotic catheter head. The horizontal span can separately connect the pair of vertical spans and the first robotic catheter head can be configured to operably connect or engage with the first coupler extension and the first coupler extension can be coupled to the horizontal span. The second and third robotic catheter heads can be operably connected to the horizontal span. The first and second vertical spans can be configured to releaseably couple to a patient bed. In one embodiment, the arch-shaped suspension system can further comprise a first linear guide block coupled to the first vertical span and a second linear guide block coupled to the second vertical span. The first and second linear guide blocks can be configured to attach to a pair of extension members coupled to the patient bed. In another embodiment, the pair of extension members can each comprise a round linear guide rail and the first and second linear guide blocks can be configured to move along the pair of round linear guide rails.

In yet another embodiment, an apparatus is provided that includes one or more robotic catheter heads configured to respectively actuate one or more catheters or other medical devices. The apparatus includes a catheter suspension structure configured to receive the robotic catheter head(s), and further includes a plurality of mounting legs configured to support the catheter suspension structure above a supporting platform to which the mounting legs are directly or indirectly attached. In a particular embodiment of such an apparatus, the mounting legs may be discrete members coupled to the catheter suspension structure, while in other embodiments the mounting legs may be integrally coupled to the catheter suspension structure. In one particular embodiment of such an apparatus, the mounting legs and the catheter suspension structure collectively provide an arch-shaped suspension structure affixed to the supporting platform to form an opening through which a patient passes through on the supporting platform.

BRIEF DESCRIPTION OF THE DRAWINGS

FIG. 6 is an isometric view of one embodiment of a linear guide rail and a linear guide block.

FIG. 7 is an isometric view of another embodiment of a linear guide block.

FIG. 8 is an isometric view of another embodiment of a linear guide rail.

FIG. 9 is an isometric cross-sectional view of another embodiment of a linear guide block.

DETAILED DESCRIPTION

Various representative embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1:
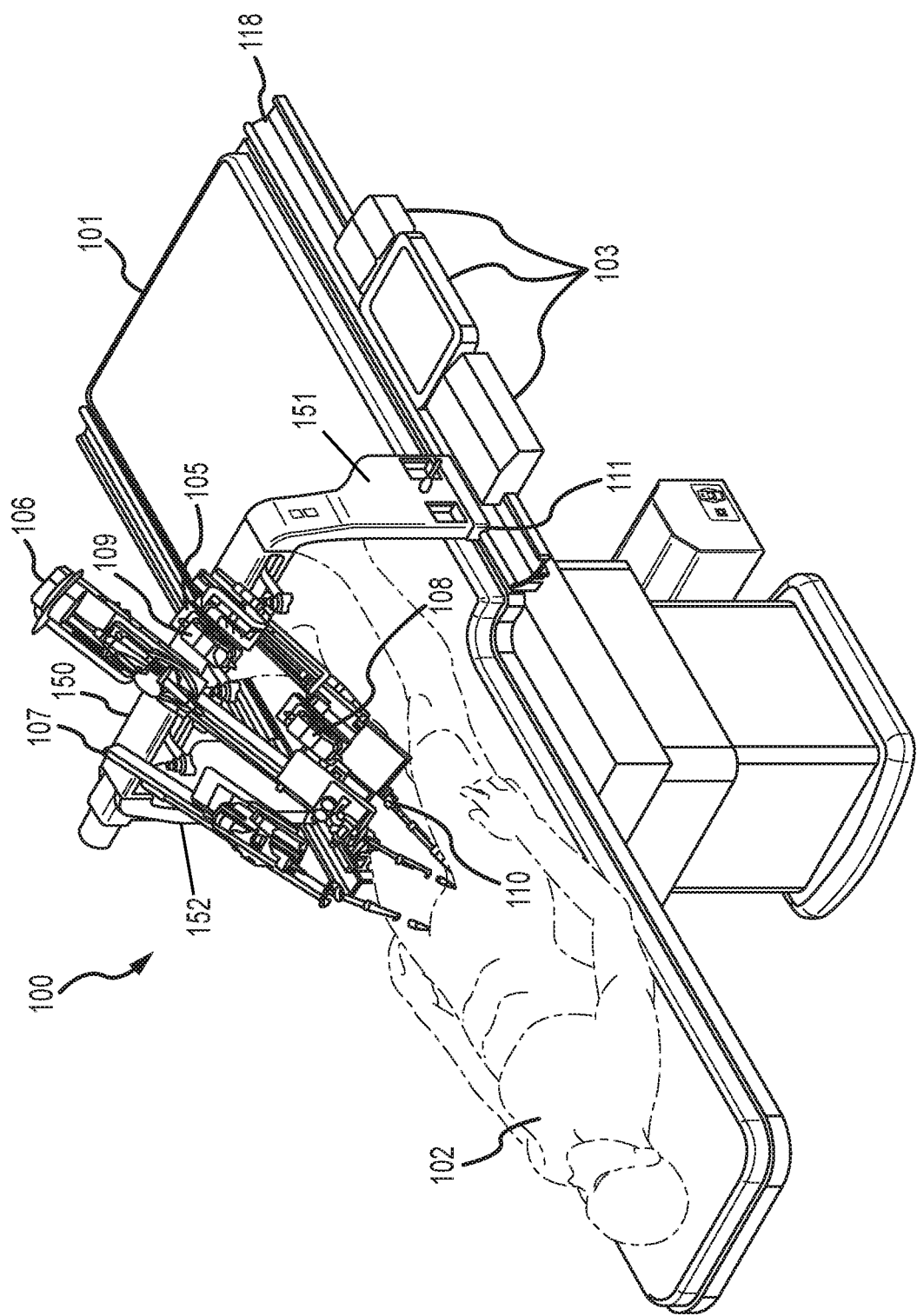
FIG. 1 is an isometric view of a robotic catheter system in use on a patient.

FIG. 1 illustrates one embodiment of a suspension system for a robotic medical system, such as a Remote Catheter Guidance System (RCGS) for navigating a robotic catheter within a body 102. The suspension system may be structurally maintained over the body 102 and/or patient table 101 such that at least a portion of the suspension system has a segment(s) passing over the patient's body that is supported at a plurality of points about the patient's body 102. A suspension system having multiple mounting points provides stability, particularly when coupled to one another via integral or intermediate beams or other structures to enable the system to be suspended over the patient table 101 and body 102.

In the illustrated embodiment, the suspension system is an arch-shaped suspension system 100 slidably mounted to a set of extension members 118 that are mounted to a patient table 101. The illustrated arch-shaped suspension system 100 comprises at least two vertical spans 151, 152 and a horizontal span 150 between them. While the at least two vertical spans 151, 152 and the attached horizontal span 150 in the illustrated embodiment comprise mostly straight sections coupled to each other at around 90 degrees there is no requirement that the arch-shaped suspension system 100 take this exact shape. The support members of the arch-shaped suspension system 100 can be comprised of a continuous transition from upright to horizontal. The spans also have no requirement that they are straight and do not have to be completely perpendicular to the horizontal and vertical planes. Moreover, the support members can include various embodiments comprising various shapes where the suspension system is attached at each side of the patient table 101 and the support members comprise connected or otherwise integrated structural portions generally rising from the patient table 101. The various shapes can include e.g. a continuously curved shape, an M-shaped structure, a trapezoidal shaped structure, or the like.

The arch-shaped suspension system 100 can further comprise a linear guide block 111 to allow movement along the set of extension members 118 at the sides of the patient table 101 and at least one robotic catheter head 110 (e.g., a first robotic catheter head 105, a second robotic catheter head 106, and a third robotic catheter head 107 as shown in the example of FIG. 1) attached to the horizontal span 150 of the arch-shaped suspension system 100. The arch-shaped suspension system 100 allows for the RCGS to be moved freely over the patient table 101 with no interference from parts of the system as it is moved over the body 102. In the illustrated embodiment the first robotic catheter head 105 is configured to actuate a robotic catheter cartridge 109 which is introduced to the body 102 through a robotic sheath cartridge 108, the second robotic catheter head 106 is configured to actuate a rotatable mapping catheter 113, and the third robotic catheter head 107 is configured to actuate an ultrasound catheter 114. It should be understood, however, that the arch-shaped suspension system 100 can use a wide variety of medical devices within the body 102 for diagnosis or treatment. Further, it should be understood that the arch-shaped suspension system 100 may be used to navigate medical devices used in the diagnosis or treatment of portions of the body 102 other than cardiac tissue.

In another embodiment, a control panel (not shown) can be operably coupled to the suspension system. The control panel can comprise a small LCD, a touchscreen, or discrete buttons. The control panel can be attached directly to or operably coupled with the suspension system. The control panel can be used to control certain features of the robotic system while the user is adjacent the patient table 101. The control panel can be used to initially set up the system and place the distal end of the robotic sheath cartridge 108 and the robotic catheter cartridge 109 within the body 102. The control panel can also be used to initiate a homing procedure where the limits of travel for the various robotic catheter heads 110. The control panel can also be used to set the starting position of the translation rail for each robotic catheter head 110.

In yet another embodiment, an arch-shaped suspension system comprises an electrical routing system (not shown) and can include other internal conduits or external features to facilitate the connection of the RCGS to a control station or to pass equipment 102, such as medical equipment through the RCGS. In one embodiment the RCGS comprises conduits through which electrical wires, cables, saline lines, and other equipment 103 can be passed through before or during a procedure. In a separate embodiment, the RCGS comprises internal conduits with connectors located externally to connect various electrical wires, cables, saline lines, and other equipment 103 to the system. These embodiments of the arch-shaped suspension system would minimize the distribution of cables dragging around the arch-shaped suspension system and the patient table and minimize entanglement of the various components during procedures.

Figure 2:
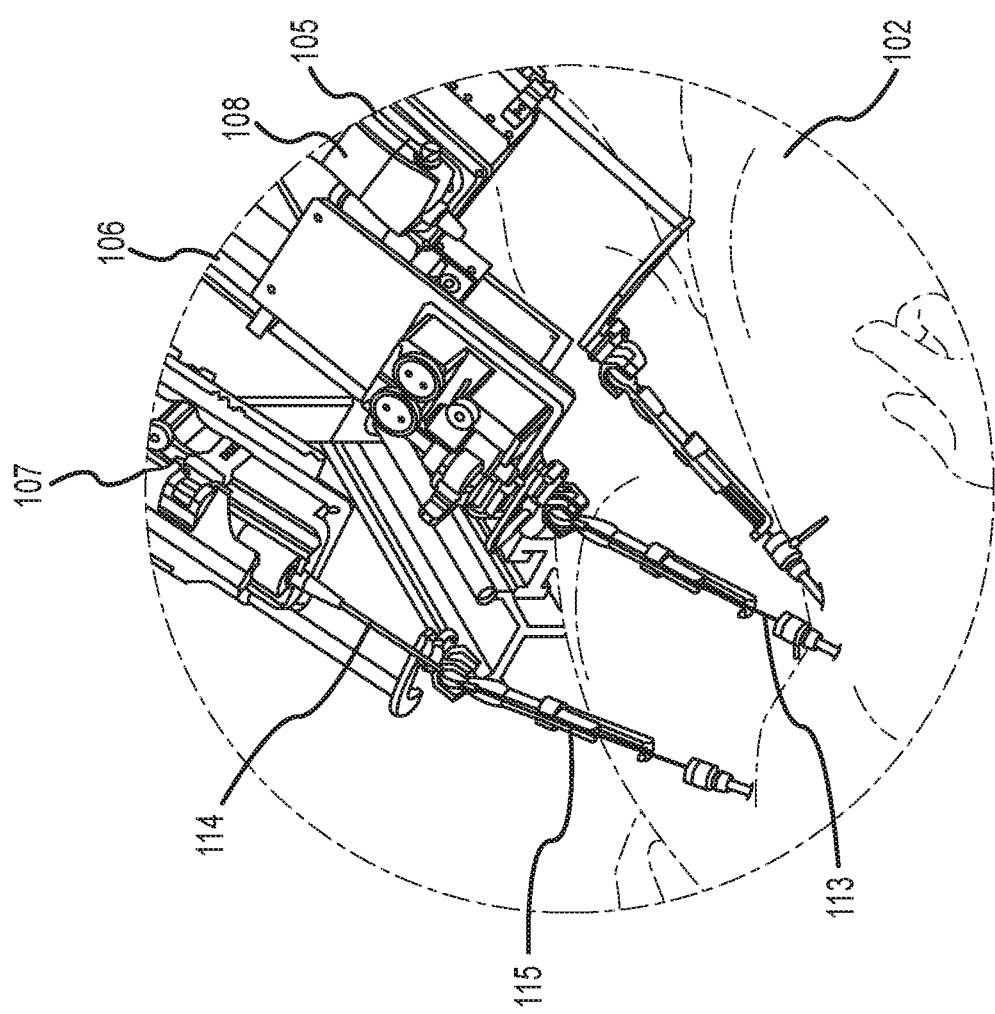
FIG. 2 is an enlarged isometric view of a distal end of a set of robotic catheter heads and their associated medical devices being used in a procedure.

FIG. 2 is an enlarged view of the circled region of FIG. 1, depicting a distal end of the first 105, second 106, and third 107 robotic catheter heads. FIG. 2 illustrates the area of entry of the medical devices into the body 102. The medical devices are positioned and supported by an adjustment support 115 which can keep a proximal end of the medical device that is outside the body 102 from kinking or otherwise moving when advancing or retracting the medical device from the body 102 or actuating a distal end of the medical device during a procedure.

Figure 3:
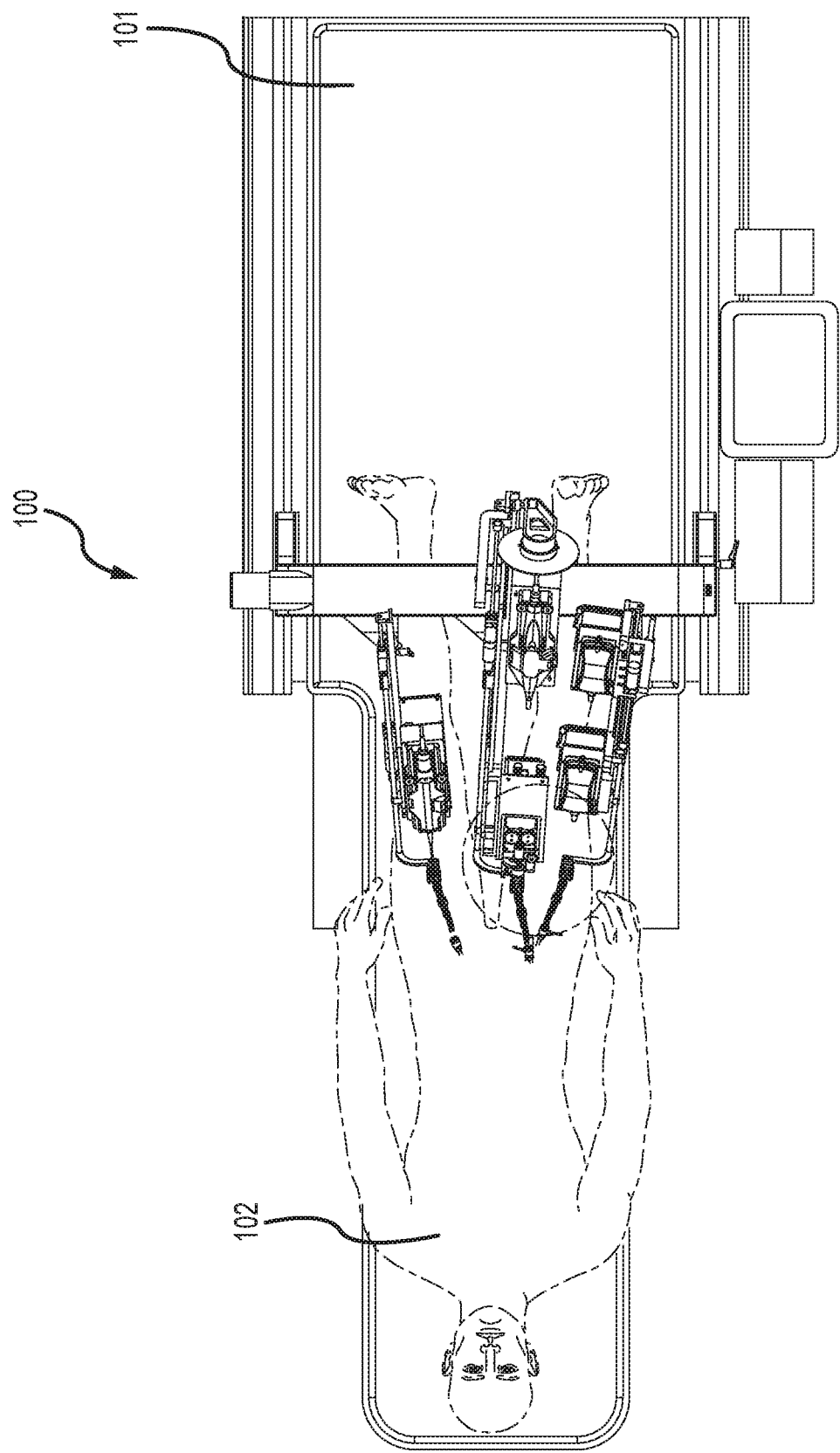
FIG. 3 is a top view of the robotic catheter system in use on a patient.

FIG. 3 depicts a top down view of the embodiment of the suspension system depicted in FIG. 1.

Figure 4:
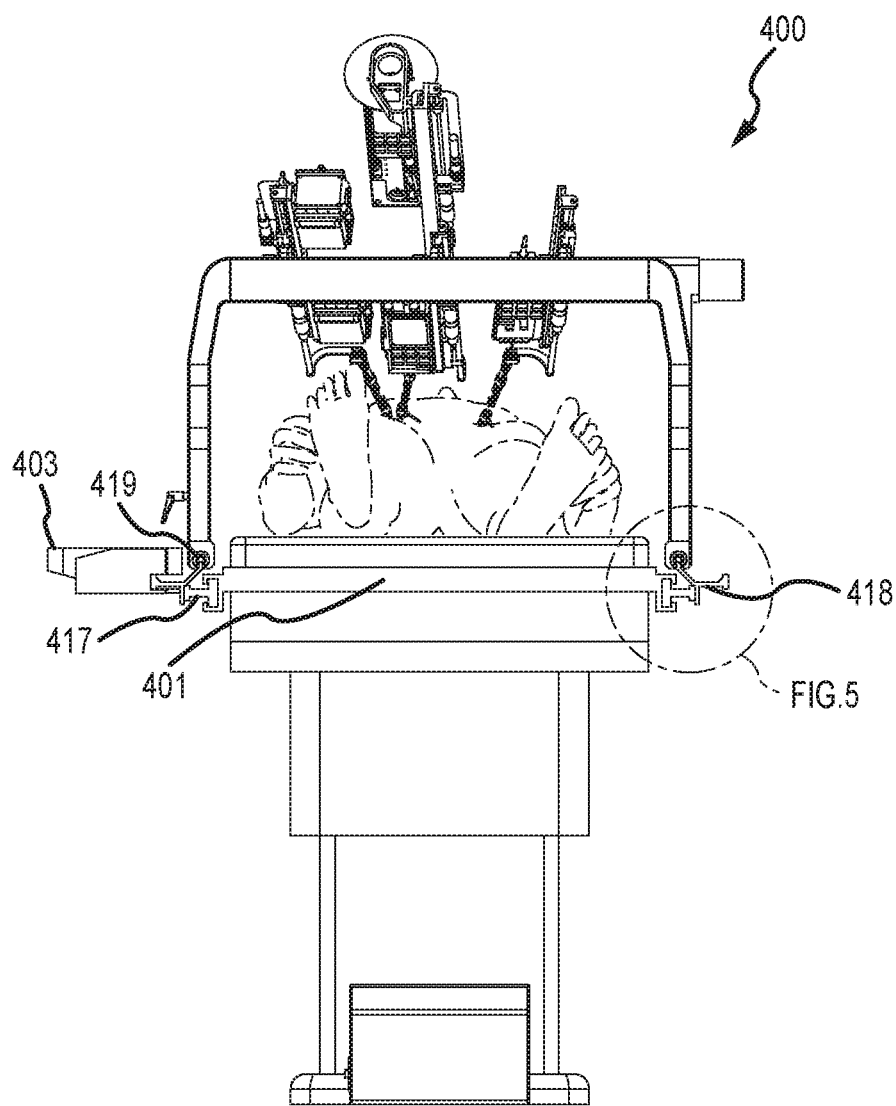
FIG. 4 is a side view of a robotic catheter system in use on a patient.

FIG. 4 illustrates an embodiment of the suspension system for an RCGS and depicts a side view of the system. This view illustrates the arch-shaped suspension system 400 and its ability to slide freely over the sides of the patient table 401. The arch-shaped suspension system 400 can be securely mounted directly to the bed rails 417 attached to the patient table 401. However, during some procedures multiple pieces of equipment 403 can already be attached to the bed rails 417. This equipment 403 can be attached to the bed rails 417 in various unknown locations and could make it difficult to ensure that specific locations along the bed rails 417 are available to mount the arch-shaped suspension system 400. If enough pieces of equipment 403 are already attached to the bed rails 417 it is also possible that there is no extra space to mount the arch-shaped suspension system 400.

The current embodiment depicts a set of extension members 418 that have been mounted along both existing longitudinally extending patient bed rails 417. The extension members 418 are parallel to the original bed rails and in one embodiment are at the same approximate height as the bed rails 417. The equipment 403 that had been attached to the bed rail 417 can be moved to the extension member 418. The extension member 418 can then include mount points 419 for the arch-shaped suspension system 400. The arch-shaped suspension system can then be unobstructedly moved over the extension members 418. This embodiment allows the position of the arch-shaped suspension member 400 to be adjusted along the entirety of the extension members 418 so that the RCGS can be aligned with the position that is required for the system's use, whether this position be for use on a patient during a procedure or moving the system to the side so that unobstructed access may be gained to the rest of the patient table 401.

Figure 5:
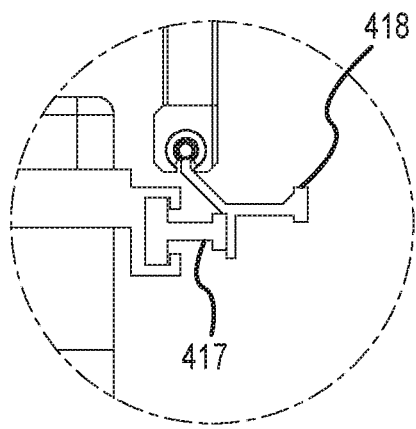
FIG. 5 is an enlarged side view of a patient table extension member and a linear guide block slideably coupled to the extension member.

As seen in FIGS. 4 and 5 the extension members 418 can comprise a rail system. The rail system can comprise a linear guide rail 430 coupled to each extension member 418. The system can further comprise linear guide blocks 432 coupled to the arch-shaped suspension system. In this embodiment the linear guide blocks 432 are configured to be slideably moveable along the linear guide rail 630. Examples of guide rails that can be coupled to an extension member include: round guide rails, square guide rails, wheeled guide rails, and bushing type guide rails among others. Preferably, the wheeled guide rails could be used due to that designs relative insensitivity to environmental conditions such as light damage, dirt, and debris that may be present in the environment where the arch-shaped suspension system can be used.

In another embodiment the arch-shaped suspension system can comprise rails operably coupled to one or both of the vertical spans. The arch-shaped suspension system rails can facilitate the attachment of accessory equipment, e.g. a saline pump, an ablation generator, ECG monitor, or the like, to the arch-shaped suspension system.

FIG. 6 illustrates an alternative embodiment of a linear guide rail 630 and a linear guide block 632. A plurality of mounting holes 634 can be seen on the linear guide block 632 which allow for secured coupling of the linear guide block 632 with an arch-shaped suspension system. A linear guide track 631 can also be seen on the linear guide rail 630. The linear guide track 631 is of a shape that allows for secure coupling of a linear guide block 632 by a guide housing 633. The linear guide block 632 in this embodiment can include wheels or other mechanisms shaped to conform to the linear guide track 631.

FIG. 7 illustrates another alternative embodiment of a linear guide block 732. The guide housing 733 of the linear guide block 732 in this embodiment can be paired with a round linear guide rail to allow for unobstructed movement of an arch-shaped suspension system. A plurality of mounting holes 734 can be seen on the linear guide block 732 which allow for secured coupling of the linear guide block 732 with the arch-shaped suspension system.

FIG. 8 illustrates another alternative embodiment of a linear guide rail 830 with a linear guide track 831.

FIG. 9 illustrates an isometric cross section of an alternative embodiment of a linear guide block 932. The linear guide block 932 can comprise a guide housing, 933 a roller 935 which can be configured to move along a linear guide rail, and at least one mounting hole 934 for attaching the linear guide block 932 to an arch-shaped suspension system.

Figure 10:
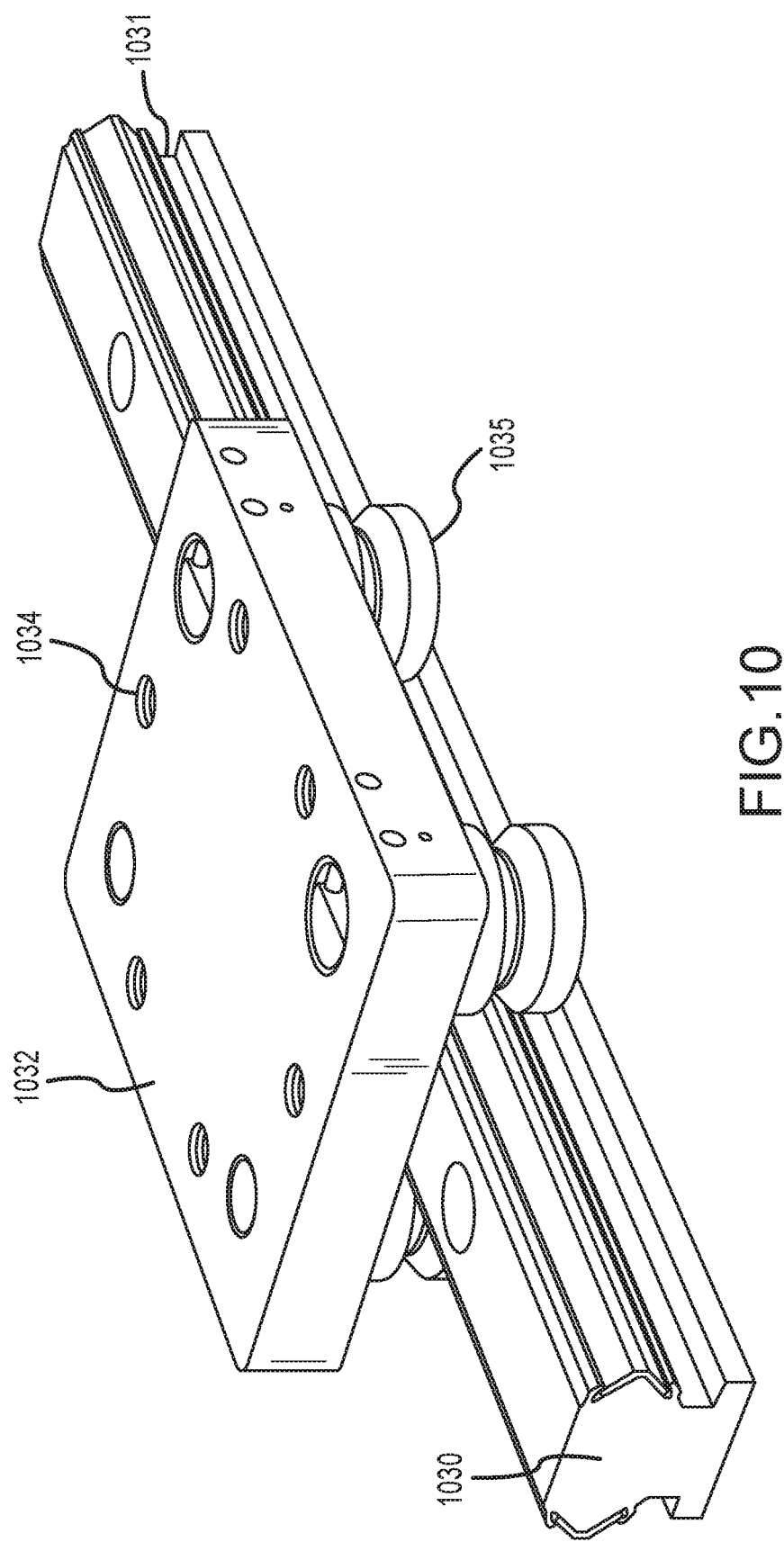
FIG. 10 is an isometric view of another embodiment of a linear guide rail and a linear guide block.

FIG. 10 illustrates an alternative embodiment of a linear guide rail 1030 and a matching linear guide block 1032. The linear guide rail 1030 comprises a linear guide track 1031 shaped to allow at least one roller 1035 to securely couple and move a linear guide block 1032 along the linear guide rail 1030. The linear guide block 1032 can include at least one mounting hole 1034 or other methods for securing the linear guide block 1032 to an arch-shaped suspension system.

Figure 11:
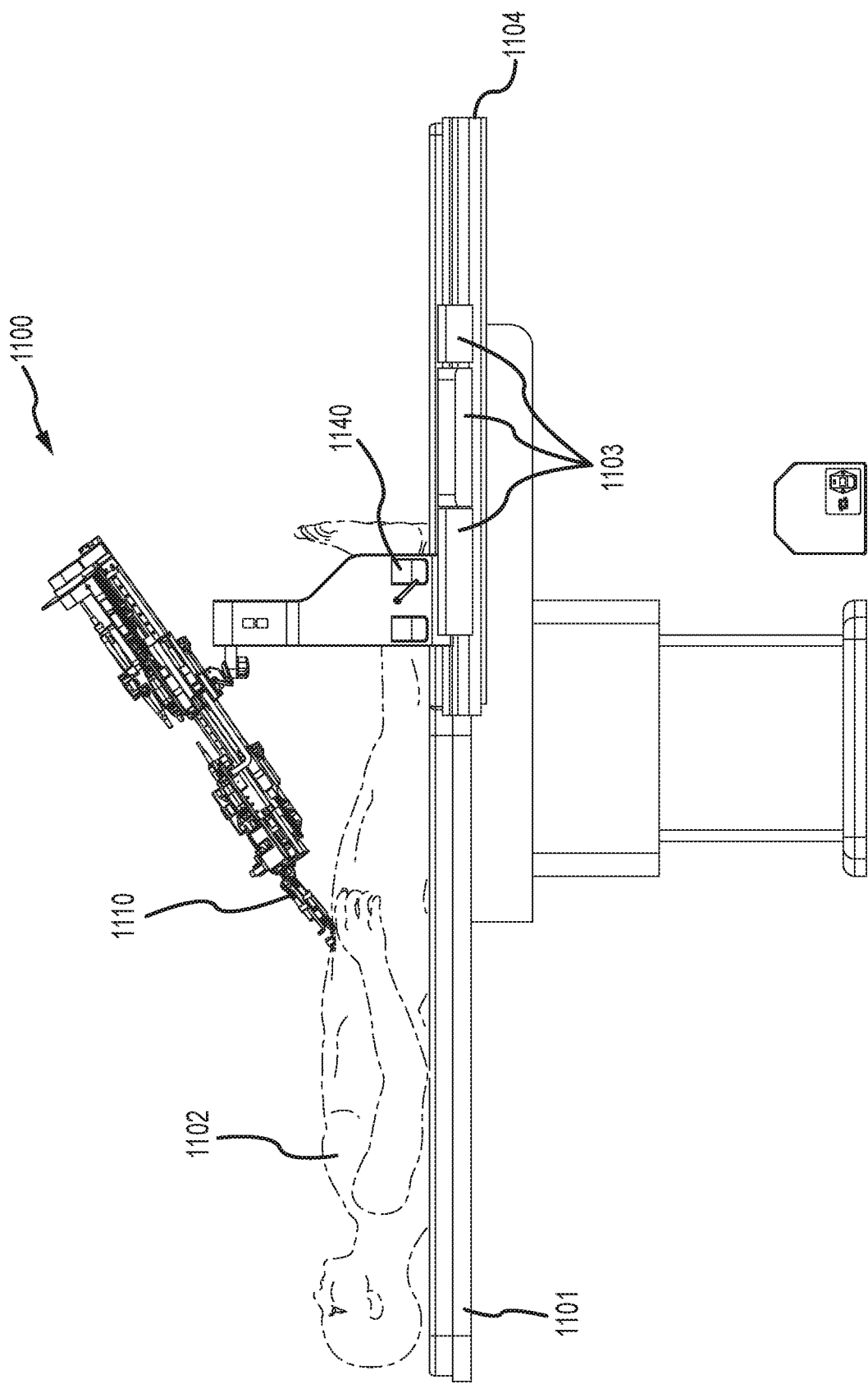
FIG. 11 is a front view of a robotic catheter system in use on a patient.

FIG. 11 depicts an embodiment of an arch-shaped suspension system 1100 for an RCGS for navigating a robotic catheter 1110 within a body 1102. This figure depicts an arch-shaped suspension system 1100 that has been aligned with a body 1102 of a patient for a procedure. The arch-shaped suspension system 1100 has been moved in to position along an extension rail 1104 coupled to the patient table 1101 and movement of the arch-shaped suspension system 1100 has not been obstructed by equipment 1103 that is attached to the extension rail 1104. Once positioned in the desired location the arch-shaped suspension system 1100 can be secured to the extension rail 1104 by at least one arch clamp 1140. The arch clamp 1140 can be released when the arch-shaped suspension system 1100 is being moved and then reengaged when a suitable location along the patient table 1101 has been found.

Figure 12:
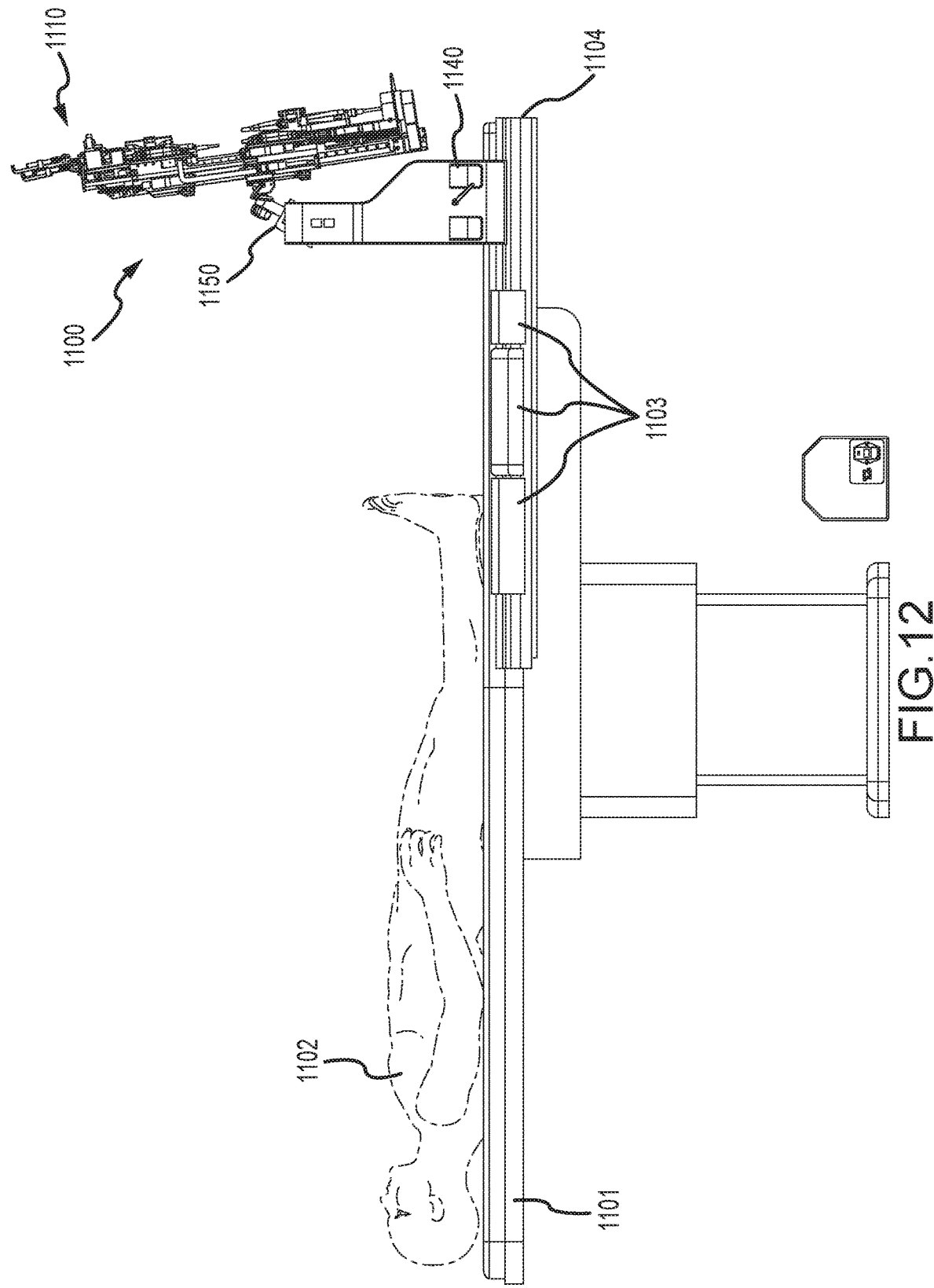
FIG. 12 is a front view of the robotic catheter system stored on an end of a patient table.

FIG. 12 depicts the embodiment of FIG. 11 where the arch-shaped suspension system 1100 has been moved to a far edge of the patent table 1101 so that the arch-shaped suspension system can be safely stored, access to the patient can be gained, or for any other reason the user may desire. The arch-shaped suspension system 1100 can include a horizontal span 1150 that can stow the robotic catheter heads in a position that is out of the way for procedures that do not require the RCGS or for times when the RCGS is not required. The horizontal span 1150 can be rotated to position the robotic catheter 1110 in a vertical fashion. This can be accomplished in a ganged fashion where all of the robotic catheter heads 1110 are rotated together, as depicted in FIG. 12, or the robotic catheter heads 1110 can be independently rotated.

The extension rails 1104 can be extended past one end of the patient table 1101 to provide a location for storage that does not require space on the patient table 1101. The space by the patient table 1101 can then be used for other equipment 1103 during procedures that do not require an RCGS. If the extension rails 1104 are extended past one end of the patient table 1101 additional support structures may be required. These support structures can include cross members or other mechanical structures to keep the extension rails 1104 at a precise separation and height from each other and to provide sufficient strength to support the arch-shaped suspension system 1100 when placed past the end of the patient table 1101.

Figure 13:
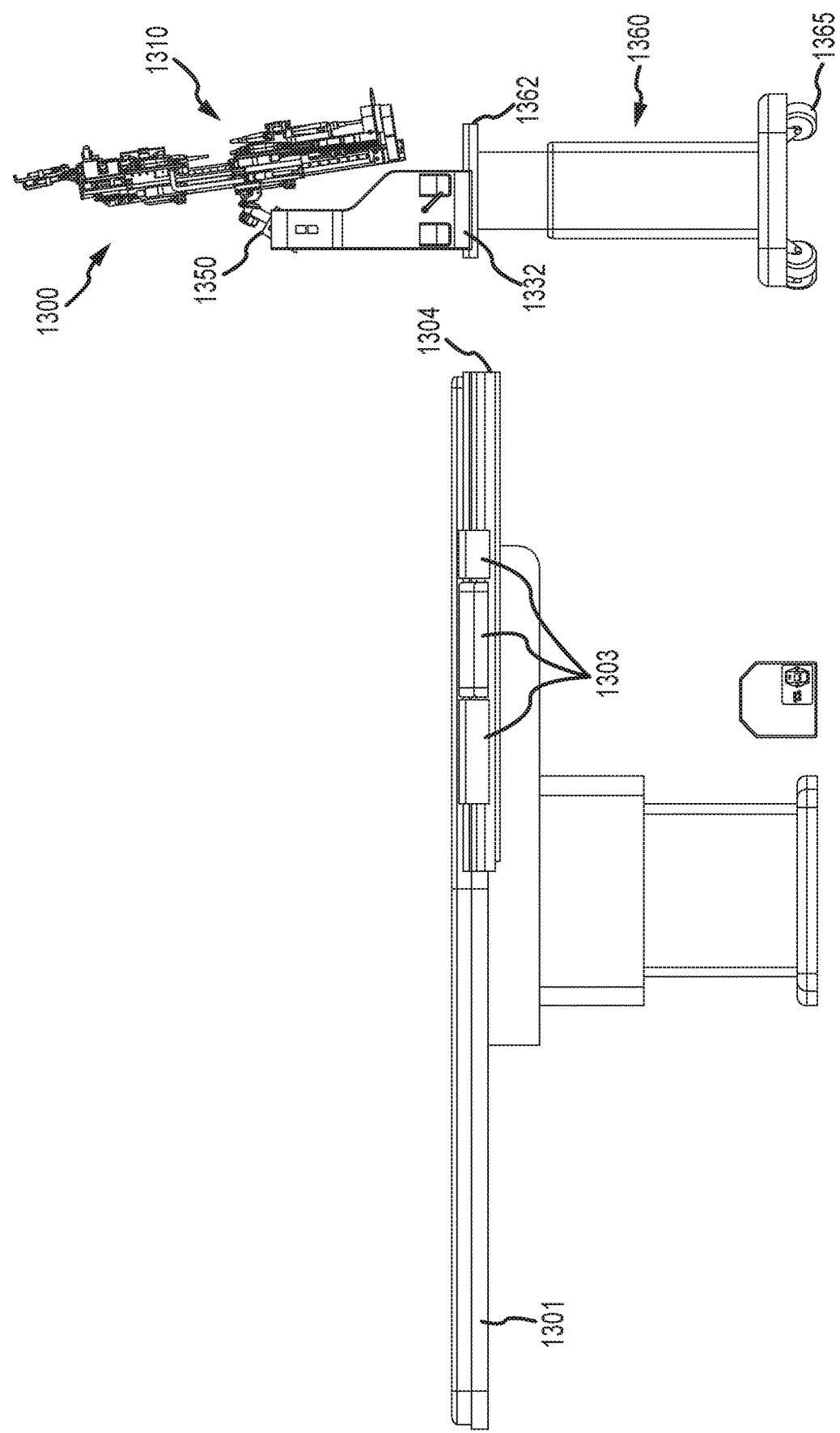
FIG. 13 is a front view of a robotic catheter system moved off a patient table and stored on an embodiment of a suspension system cart.

FIG. 13 depicts an embodiment of an arch-shaped suspension system 1300 that can be stored on a suspension system cart 1360. The suspension system cart 1360 can comprise cart rails 1362 that align with the extension rails 1304 coupled to the patient table 1301 and cart wheels 1365 or other devices to allow for movement of the system. The suspension system cart 1360 can be secured to the patient table 1301 temporarily so that the arch-shaped suspension system 1300 can be removed from the patient table 1301 for storage or other purposes. When the suspension system cart 1360 is secured to the patient table 1301, the cart rails 1362 are joined with the extension rails 1304 such that the arch-shaped suspension system 1300 can transition off of the patient table 1301 and on to the suspension system cart 1360. In one embodiment each extension rail 1304 can join with a cart rail 1362 and form an essentially continuous rail to enable the arch-shaped suspension system 1300 to be moved onto the suspension system cart 1360. However, it is not necessary that the rails join or align exactly, the arch support system can have built in tolerances in the linear guide block 1332 that still allow for the arch-shaped suspension system 1300 to be transferred to a suspension system cart 1360 when the extension rails 1304 and the cart rails 1362 are misaligned. One embodiment having low to a misalignment of an extension rail 1304 and a cart rail 1362 or to residual gaps between the extension rail 1304 and the cart rail 1362 is a wheeled rail system as seen in FIG. 10.

The embodiment of the arch-shaped suspension system 1300 shown in FIG. 13 can include a horizontal span 1350 that can stow the robotic catheter heads in a position that is out of the way for procedures that do not require the RCGS, or for times when the RCGS is not required. The horizontal span 1350 can be rotated to position the robotic catheter heads 1310 in a vertical fashion. This can be accomplished in a ganged fashion where all of the robotic catheter heads 1310 are rotated together. In some examples, equipment 1303 can be attached to the extension rail 1304 at various locations.

Figure 14:
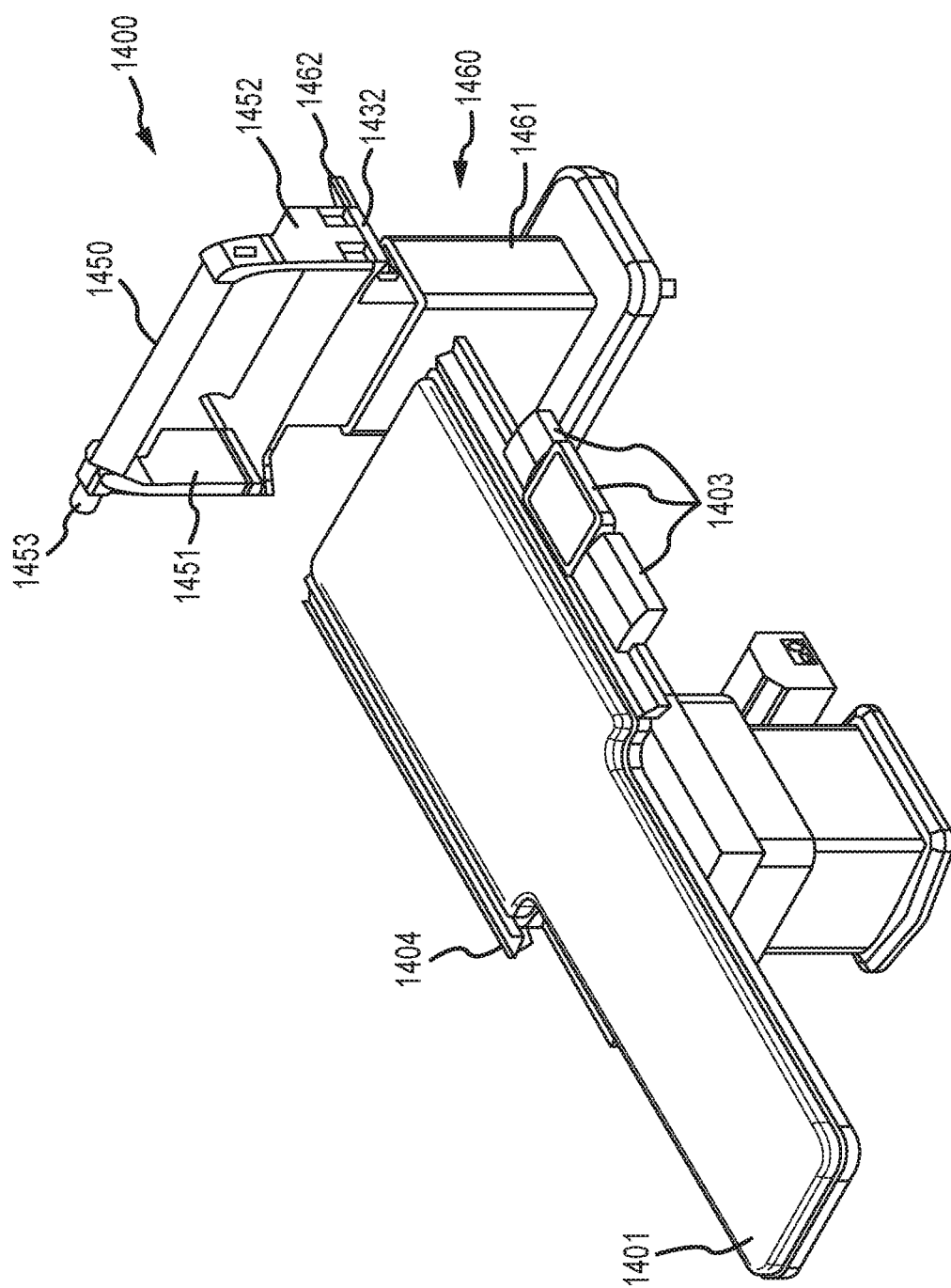
FIG. 14 is an isometric view of an arch-shaped suspension system stored on a suspension system cart.

FIG. 14 illustrates an embodiment of an arch-shaped suspension system 1400 stored on a suspension system cart 1460. The arch-shaped suspension system 1400 is shown without any robotic catheter heads attached to the horizontal span 1450. The horizontal span 1450 is shown coupled to a set of vertical spans 1451, 1452 which are each coupled to at least one linear guide block 1432. The horizontal span 1450 can be rotated by a rotation clamp 1453 that allows any attached robotic catheter heads to be rotated from a procedure position to a storage position. The storage position can be any angle, including vertical, where the robotic catheter heads are in a position conducive to storage. The arch-shaped suspension system 1400 of FIG. 14 is slideably coupled to a suspension system cart 1460. The suspension system cart 1460 comprises a set of cart rails 1462, and a cart body 1461. The cart body is of a size and shape to support and move the suspension system cart 1460 when the arch-shaped suspension system 1400 is being stored and transferred. The suspension system cart 1460 can be moved to the patient table 1401 and coupled to the patient table 1401 such that the extension rails 1404 are joined to the cart rails 1462. The arch-shaped suspension system 1400 can then be moved from the suspension system cart 1460 to the patient table 1401. The arch-shaped suspension system 1400 can then be positioned along the extension rails 1404 of the patient table 1401 without interfering with the placement of equipment 1403 that is already coupled to the patient table 1401.

Figure 15:
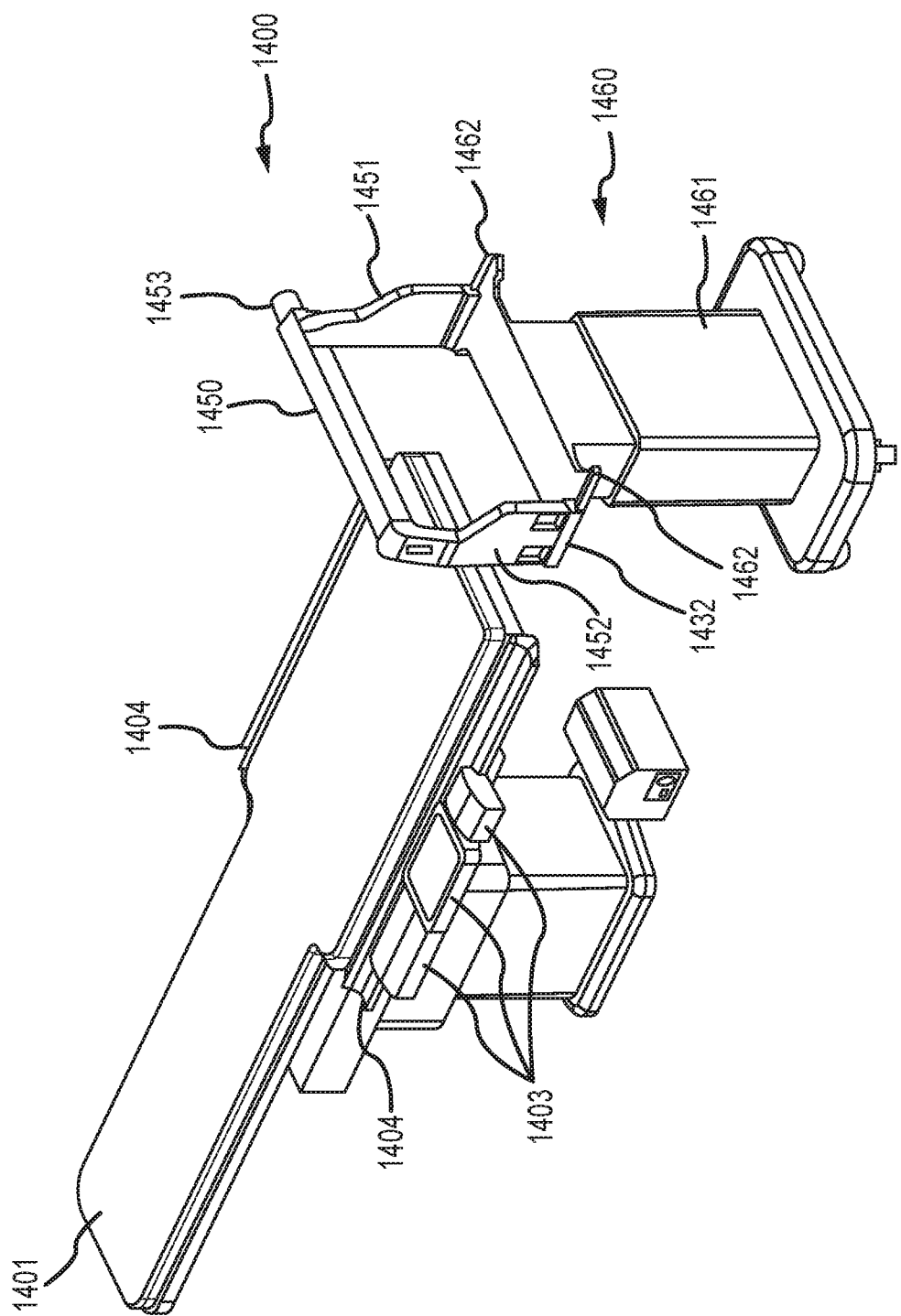
FIG. 15 is an alternative isometric view of the arch-shaped suspension system and suspension system cart seen in FIG. 14.

FIG. 15 depicts another view of the embodiment of the arch-shaped suspension system 1400, suspension system cart 1460, and extension rails 1404 depicted in FIG. 14.

Figure 16:
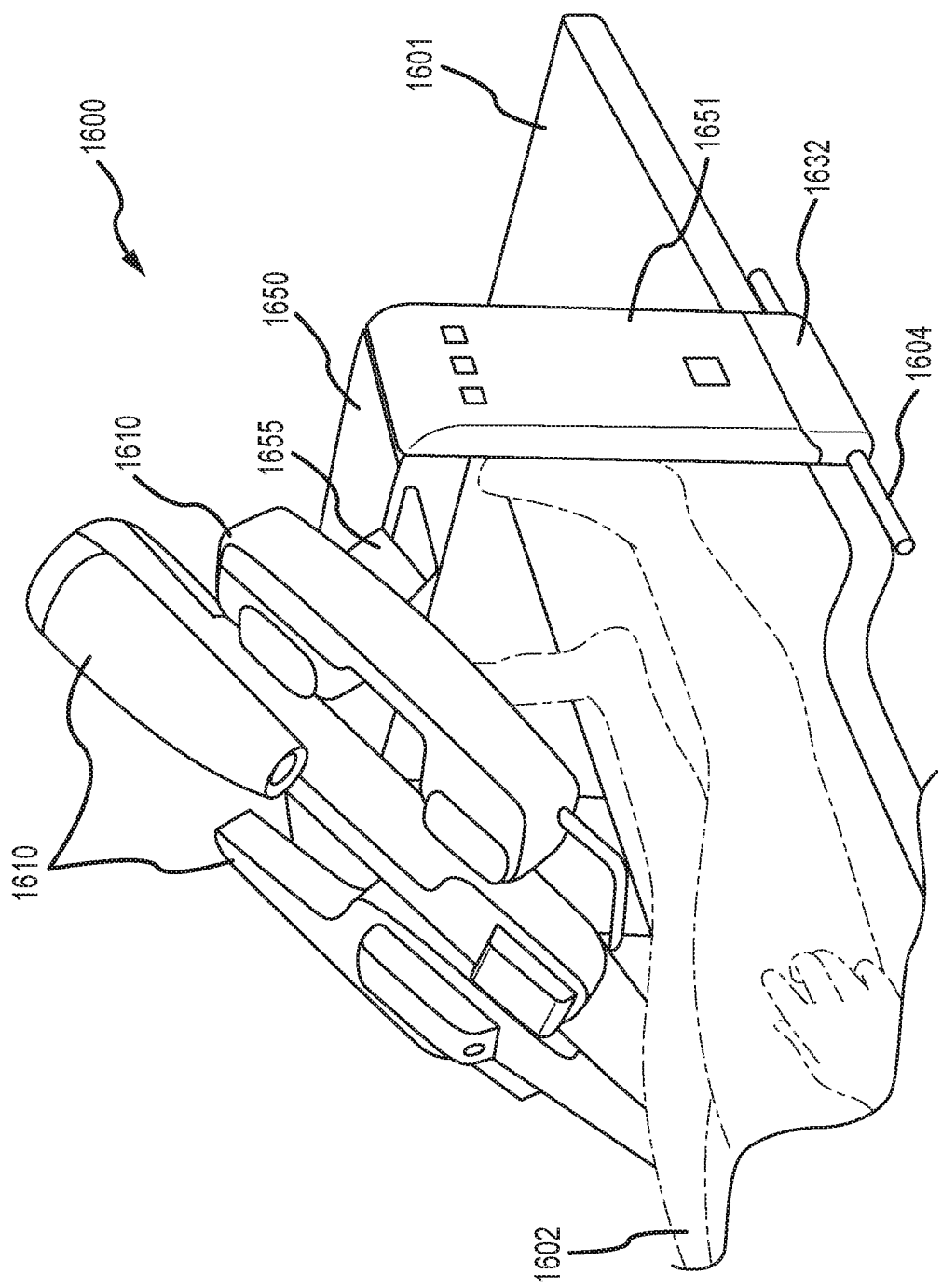
FIG. 16 is an isometric view of an alternative embodiment of a robotic catheter system.

FIG. 16 depicts another embodiment of an arch-shaped suspension system 1600 and extension rail 1604. In this embodiment the extension rail 1604 can be a bushing type guide rail and the linear guide block 1632 can be shaped in such a way to move over the bushing type guide rail. The linear guide block 1632 is coupled to a vertical span 1651 of the arch-shaped suspension system 1600. The vertical span 1651 is coupled to a horizontal span 1650 which associates with at least one robotic catheter head 1610 or other medical device by a device support 1655. The arch-shaped suspension system 1600 can slideably move along the extension rail 1604 to be positioned on the patient table 1601 where desired so that the system can have the proper access to a patient 1602.

Figure 17:
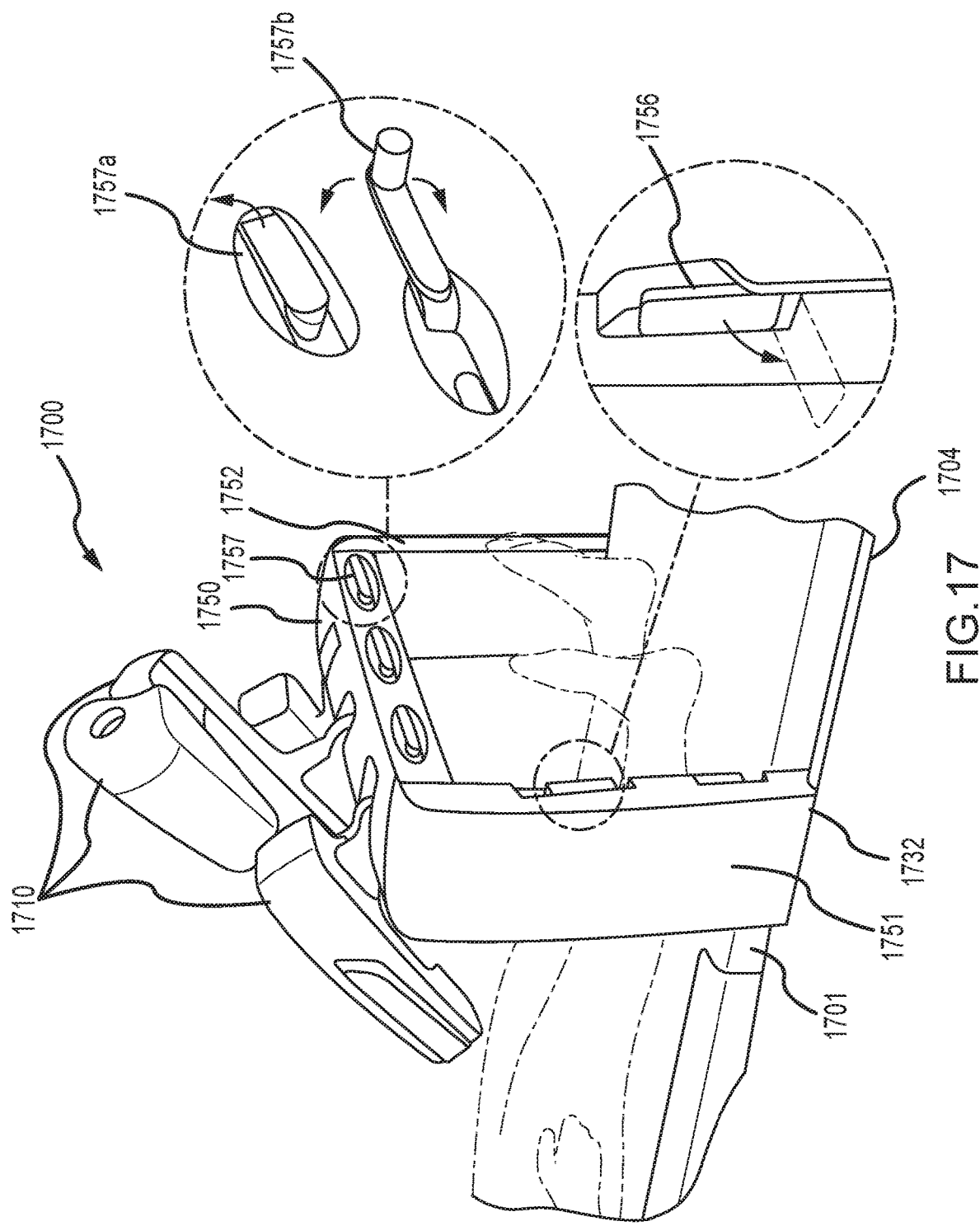
FIG. 17 is an isometric side view of an embodiment of a robotic catheter system.

FIG. 17 illustrates an embodiment of the arch support system 1700 including several sets of clamps that allow for positioning and retaining of placement for various parts of the system. The arch support system 1700 is operably coupled to a linear guide block 1732 which is slideably movable over an extension rail 1704. A vertical span 1752 of the arch support system 1700 comprises an arch clamp 1756 that enables the linear guide block 1732 to move over the extension rail 1704 when open, but secures the arch support system 1700 when closed. In another embodiment of the disclosure both vertical spans 1751, 1752 include an arch clamp 1756 and both must be released for the arch support system 1700 to move freely with respect to the table 1701.

A horizontal span 1750 of the arch support system 1700 is operably coupled to at least one robotic catheter head 1710. The horizontal span 1750 can comprise a catheter clamp 1757 for each robotic catheter head 1710 coupled to the horizontal span 1750. When open, the catheter clamp 1757b allows for free movement of the associated robotic catheter head 1710 for positioning before or during a procedure or for storage. Once the desired position of the robotic catheter head 1710 has been achieved closure of the catheter clamp 1757a can be completed. As a result, the robotic catheter heads 1710 can be adjusted based on the needs of the user both for any procedures that the RCGC may be used for and for storing the system in a way that minimizes the impact on other procedures that may occur.

Figure 18:
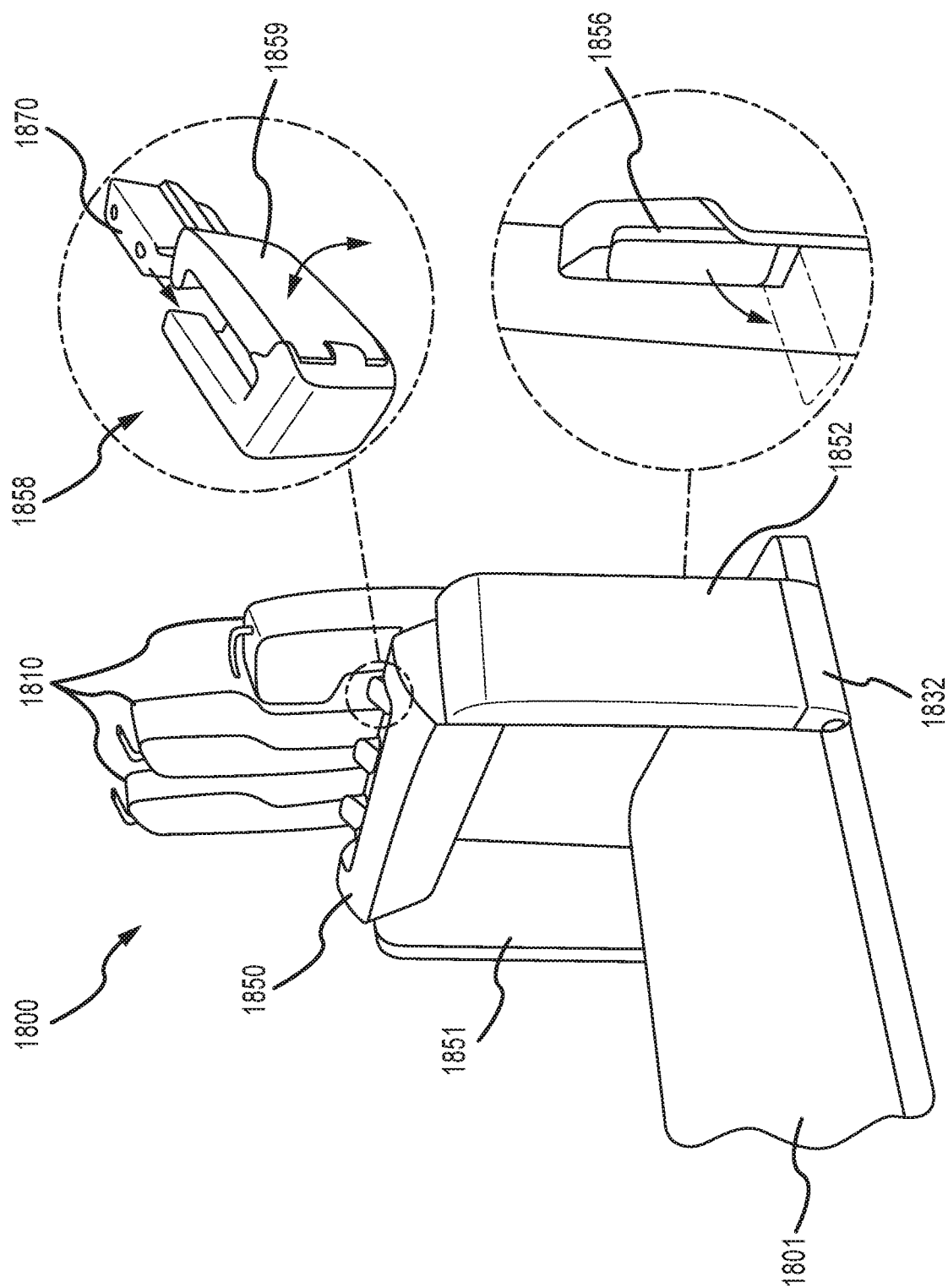
FIG. 18 is an isometric view of an alternative embodiment of a robotic catheter system positioned for storage.

FIG. 18 depicts an embodiment of an arch-shaped suspension system 1800. The pictured embodiment includes a linear guide block 1832 that is glideably movable over an extension rail (not pictured) to allow positioning of the arch-shaped suspension system 1800 in a desired position in relation to a patient table 1801. After placement at the desired position, an arch clamp 1856 positioned on one or both vertical spans 1851, 1852 can be closed so that movement of the arch-shaped suspension system 1800 is restricted. A horizontal span 1850 is operably coupled to the vertical spans 1851, 1852 and includes a mechanical method to stow the robotic catheter heads 1810 in a vertical position. The horizontal span 1850 also includes at least one robotic head coupler 1858. The robotic head coupler 1858 can comprise a coupler door 1859 which can move in relation to the rest of the robotic head coupler 1858 to allow coupling of a coupler extension 1870. Once the coupler extension 1870 has been placed within the robotic head coupler 1858, the coupler door 1859 can be closed and secured. A coupler extension 1870 can be operably coupled to a robotic catheter head 1810. By attaching at least one robotic head coupler 1858 to the horizontal span 1850 various desired robotic catheter heads 1810 can be coupled to the arch-shaped suspension system 1800. This allows a user to swap out which robotic catheter heads 1810 are available during a procedure and also to change the positioning of the robotic catheter heads 1810 if the user wishes.

Figure 19:
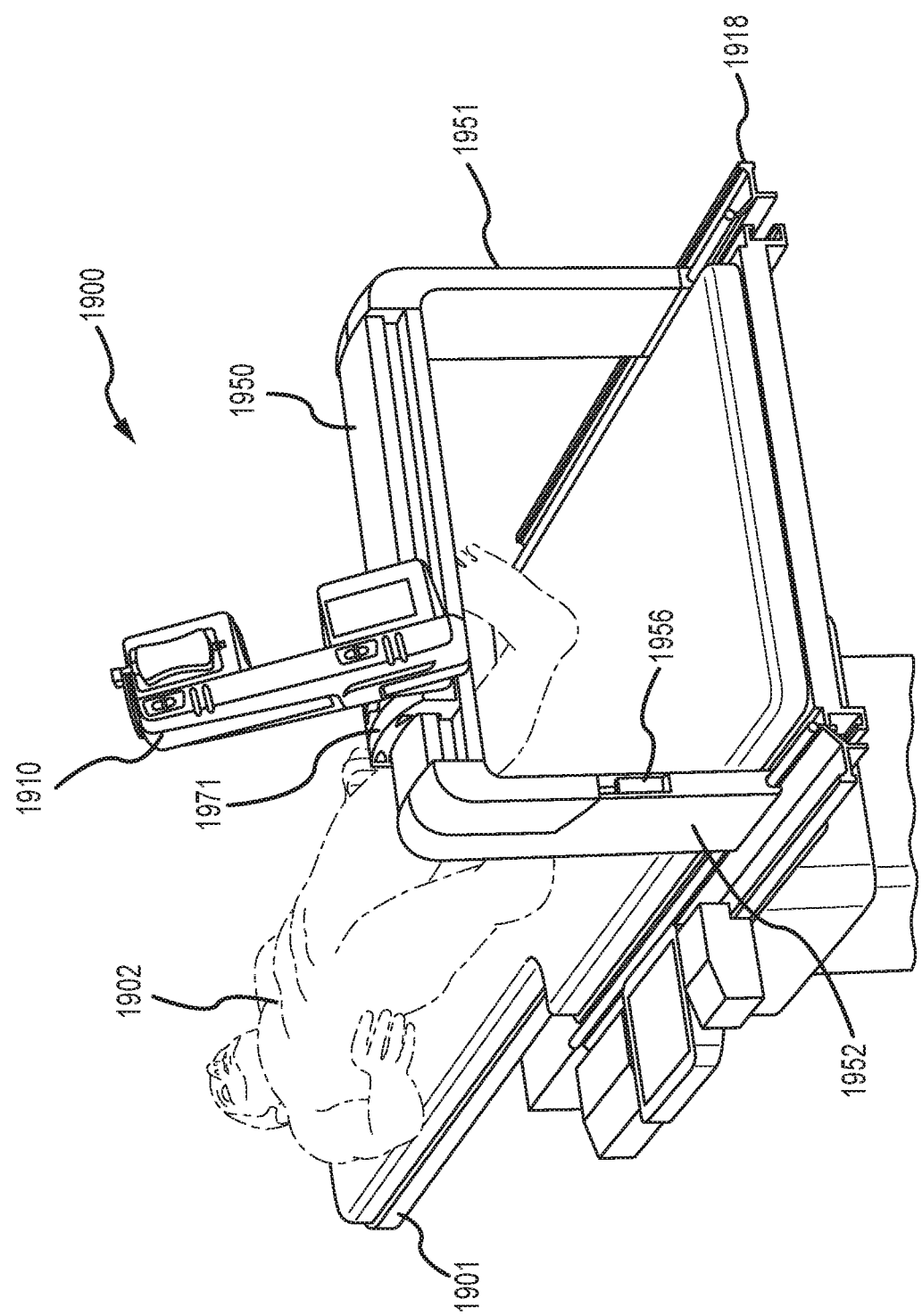
FIGS. 19-21 are isometric views of an embodiment of a robotic catheter system positioned at an end of a patient table.
Figure 20:
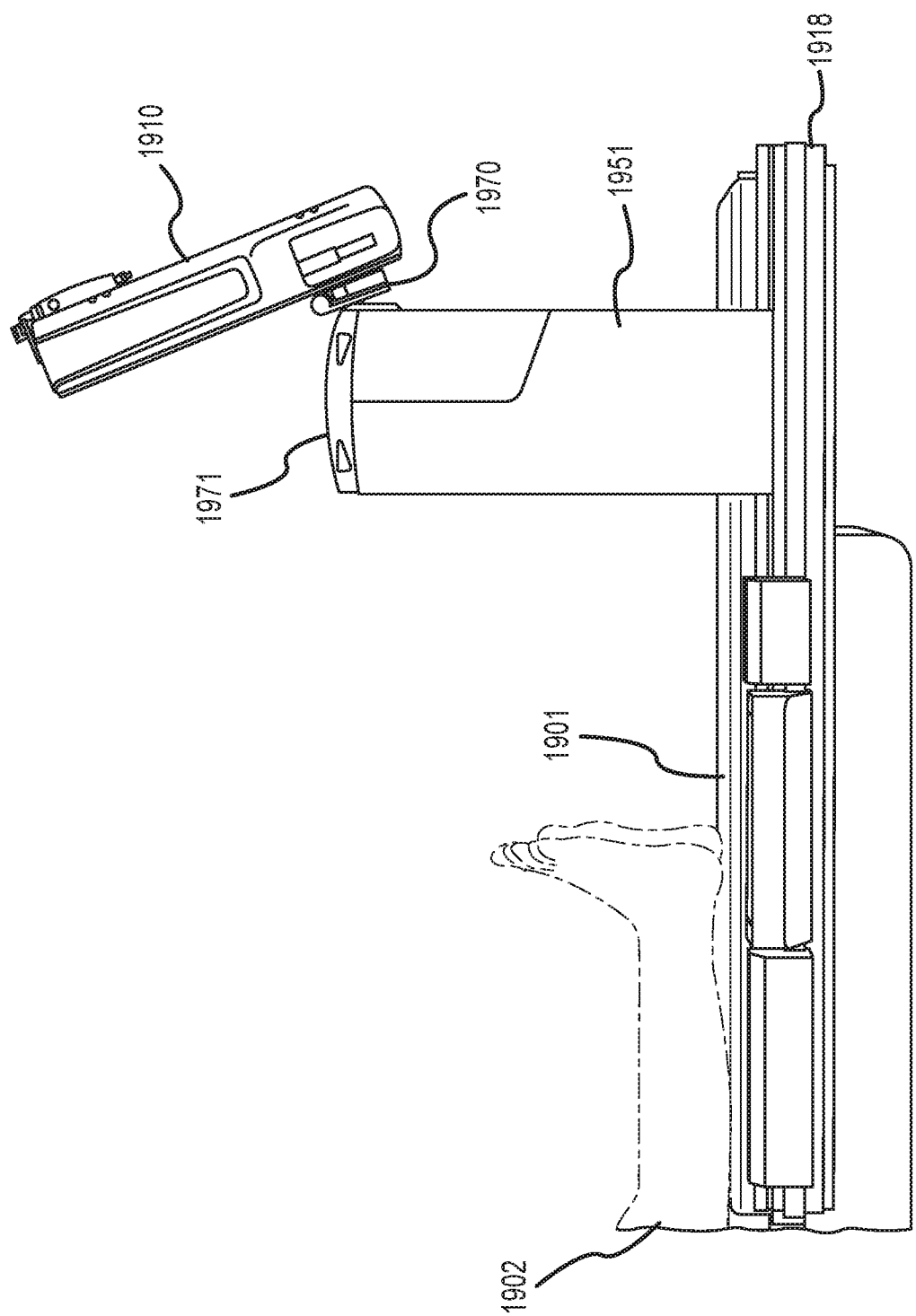
Figure 21:
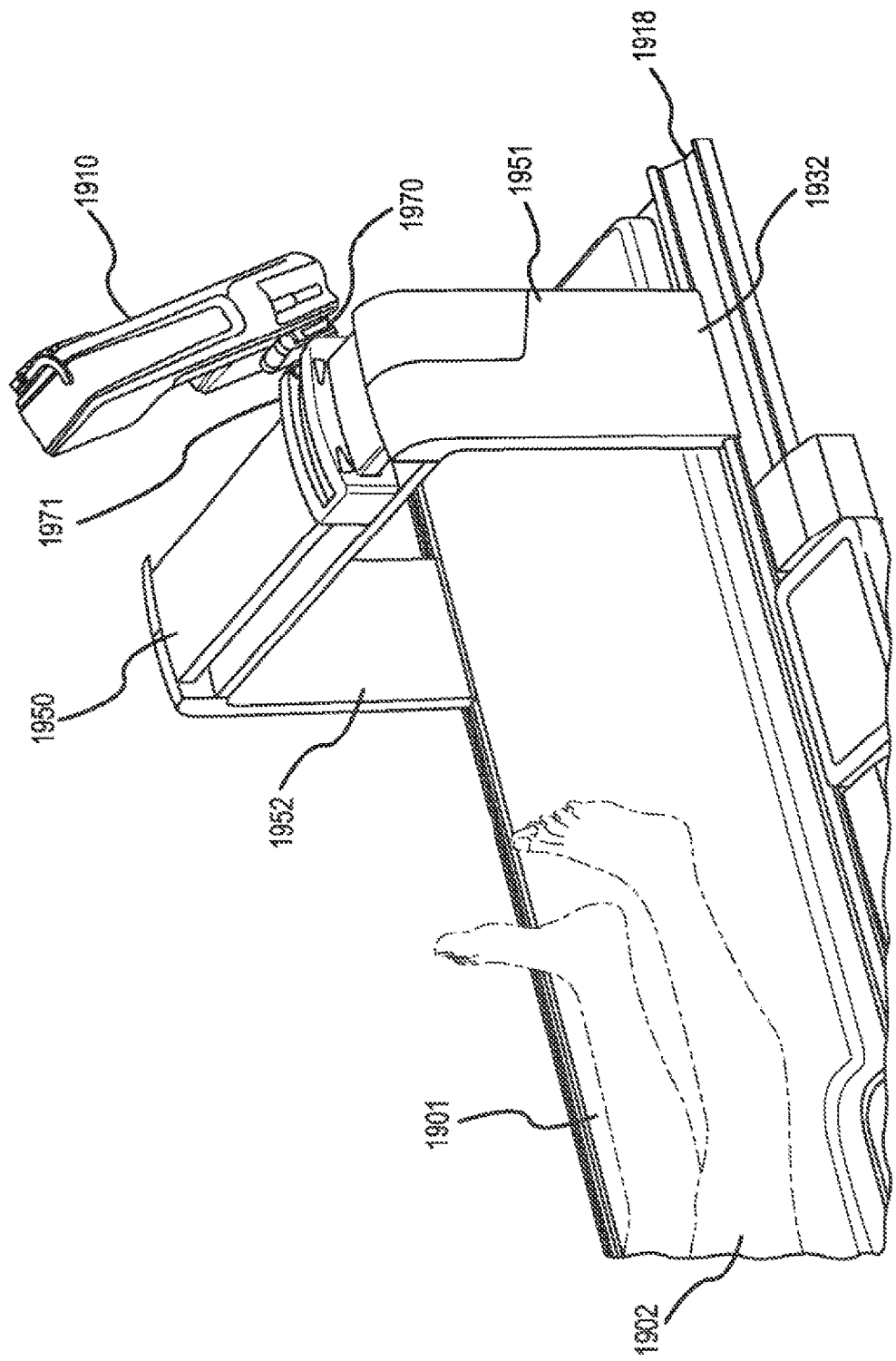

FIGS. 19-21 depict another embodiment of an arch-shaped suspension system 1900. In this particular embodiment, the arch-shaped suspension system 1900 is in a stored or preparatory position and includes a robotic mount 1971. The robotic mount 1971 allows for a robotic catheter head 1910 to removably attach to the arch-shaped suspension system 1900 by way of a coupler extension 1970. The coupler extension 1970 is attached to the robotic catheter head 1910 and facilitates movement of robotic catheter head 1910 along the robotic mount 1971. The robotic mount is movable along the horizontal span 1950 while the coupler extension 1970 is movable along a recess in the robotic mount 1971. These four directions of movement allow for precise positioning of the robotic catheter head 1910 with respect to the body 1902. These directions of movement are also independent of the ability of the arch-shaped suspension system 1900 to move along the extension member 1918 coupled to the patient table 1901 by way of at least one linear guide block attached to each vertical span 1951, 1952. The arch-shaped suspension member 1900 also can include an arch clamp 1956 that can be used to secure the linear guide block 1932 to the extension member 1918 when proper positioning has been achieved.

Figure 22:
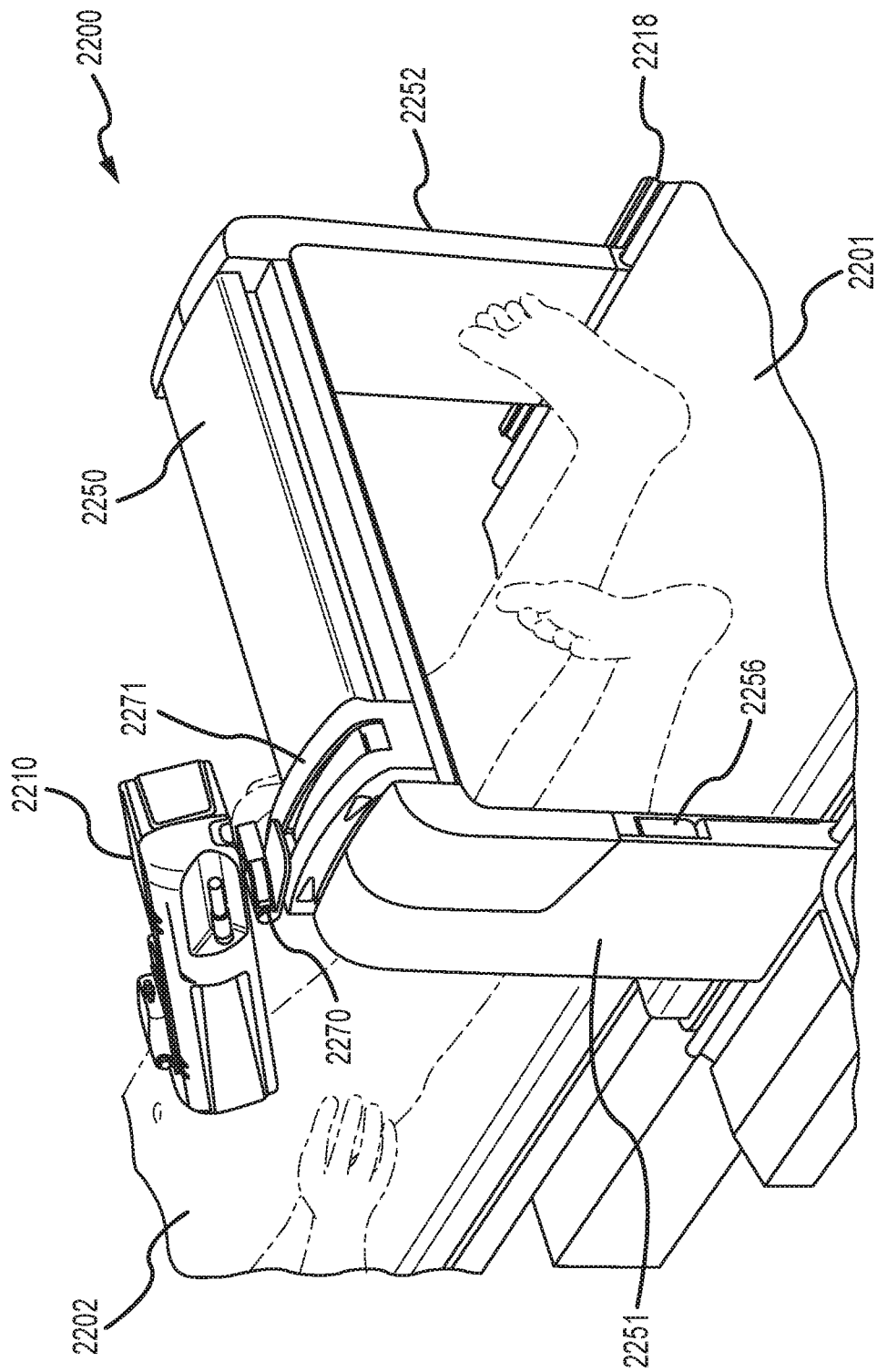
FIGS. 22-24 are isometric views of an embodiment of a robotic catheter system positioned near a patient for a procedure.
Figure 23:
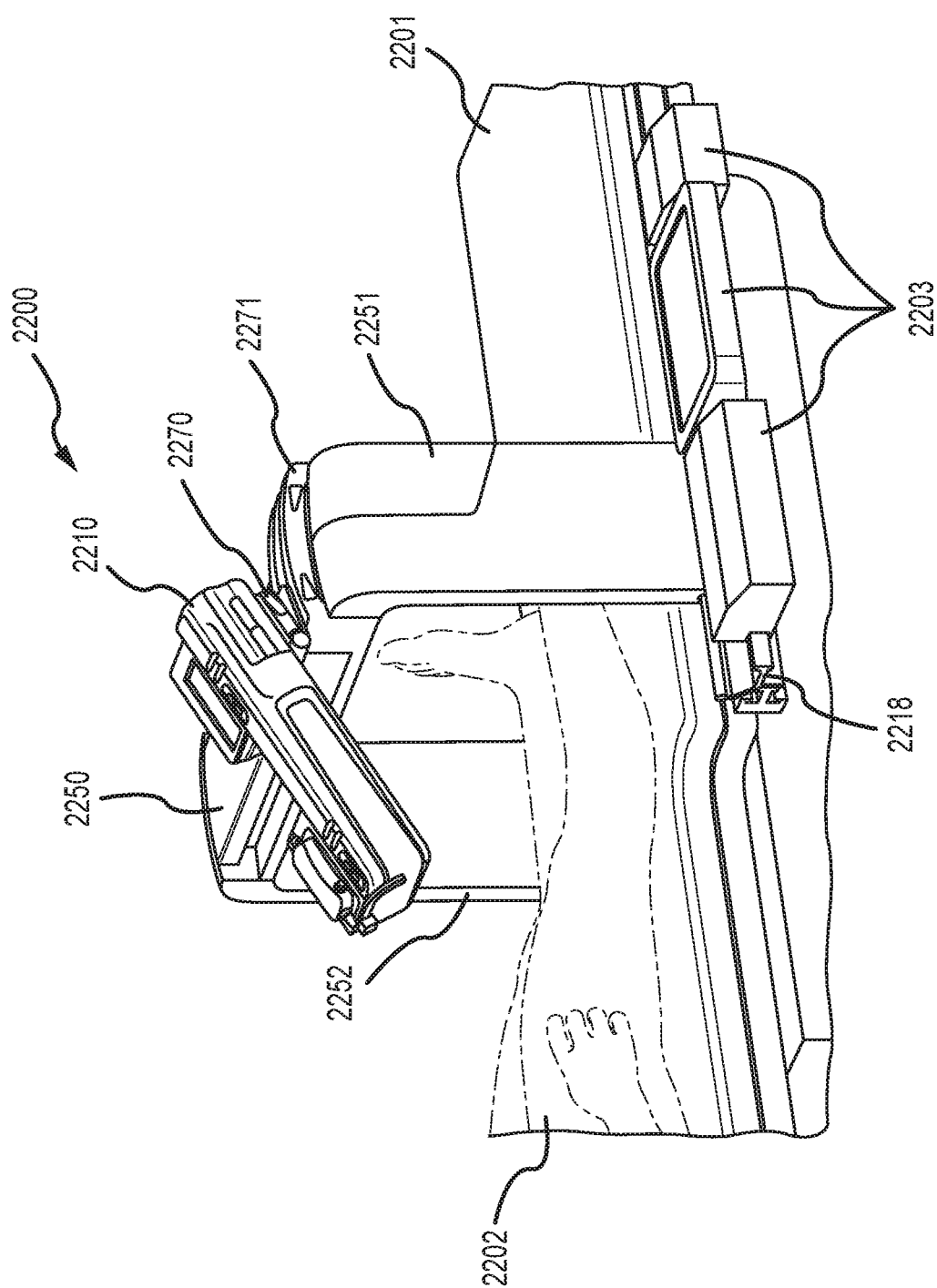
Figure 24:
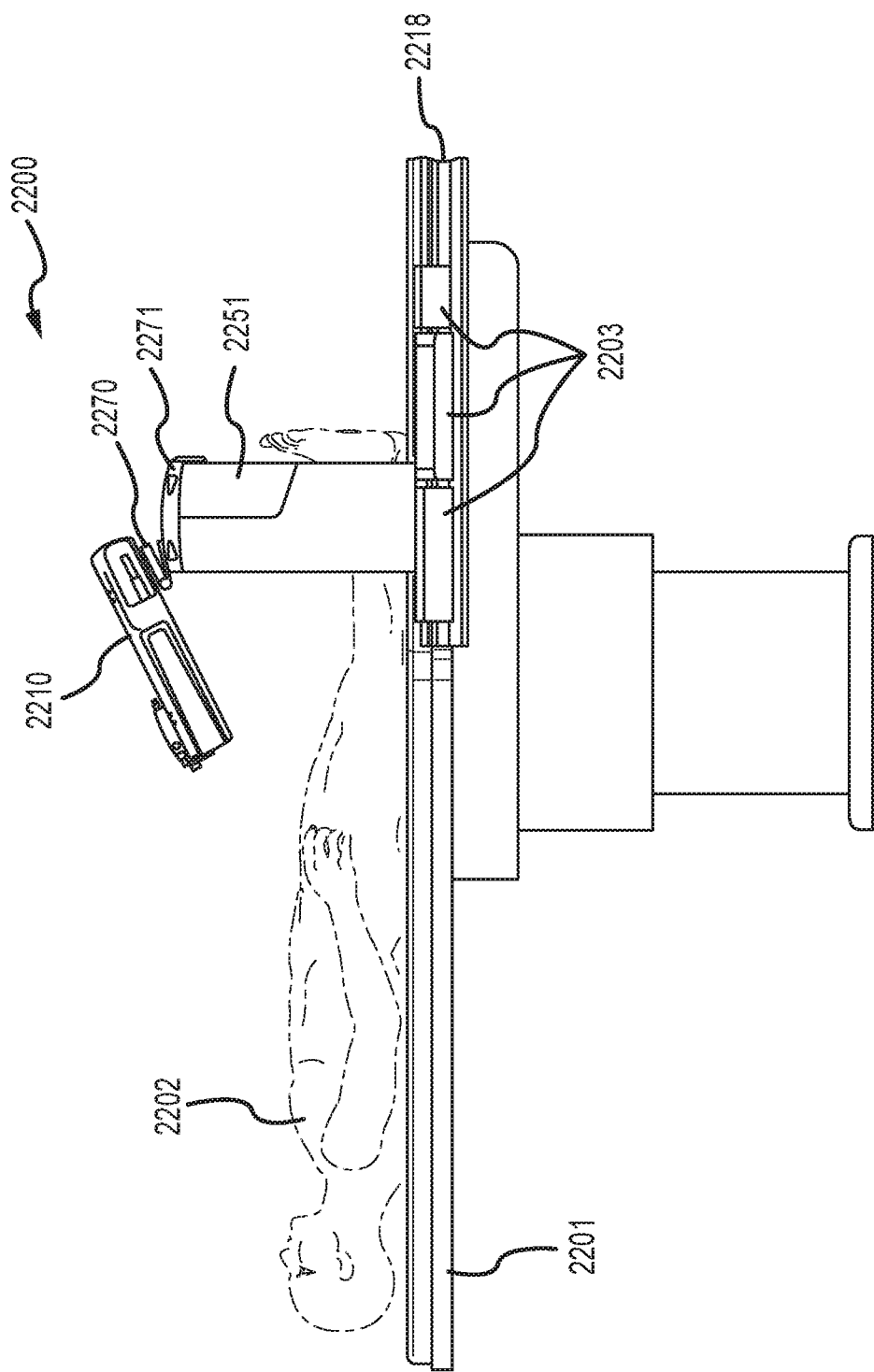

FIGS. 22-24 depict an embodiment of the arch-shaped suspension system 2200 after it has been moved into position for a procedure. In this particular embodiment, the arch-shaped suspension system 2200 has been moved forward on the extension member 2218 over the body 2202 on the patient table 2201. The extension member 2218 allowed the equipment 2203 to continue to be attached to the patient table 2201 while the arch-shaped suspension system 2200 was being moved. After proper placement of the arch-shaped suspension system 2200 was accomplished, an arch clamp 2256 can be closed, thereby securing the placement on the extension member 2218. The placement of the robotic catheter head 2210 can next be affected by moving the robotic catheter head 2210 within the robotic mount 2271, and by moving the robotic mount 2271 along the horizontal span 2250. Moving the robotic catheter head in this way allows for fine tuning of placement before or during a procedure without having to move the entire arch-shaped suspension system 2200. The coupler extension 2270 can next be used to properly align the robotic catheter head 2210 with a desired entrance location in to the body 2202. The coupler extension 2270 as shown allows for an adjustment of pitch, however other embodiments can allow adjustment of: extension, pan, rotation, pitch, yaw, etc. The pair of vertical spans 2251, 2252 allow for unobstructed movement over the patient table 2201 and over a body 2202 on the patient table 2201.

Figure 25:
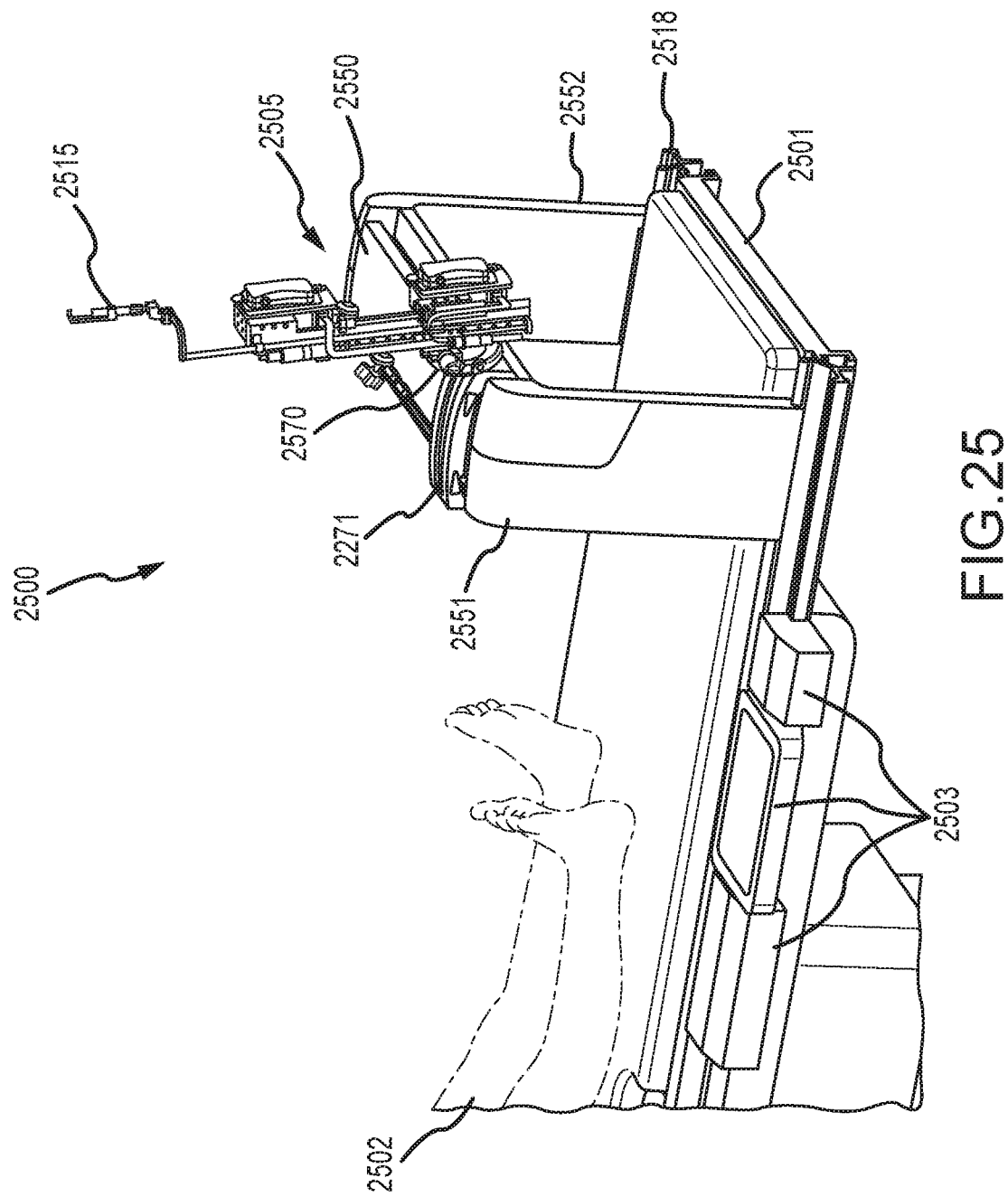
FIG. 25 is an isometric view of an alternative embodiment of a robotic catheter system stored on an end of a patient table.

FIG. 25 illustrates yet another embodiment of the disclosure. The arch-shaped suspension system 2500 can be slideably moved along the patient table 2501 with a pair of extension members 2518 that allow the arch-shaped suspension system 2500 to move without interfering with any equipment 2503 that may also be attached to the patient table 2501. The pair of vertical spans 2551, 2552 allow for unobstructed movement over the patient table 2501 and over a body 2502 on the patient table 2501. A horizontal span 2550 is coupled to the pair of vertical spans and is also slideably coupled to a robotic mount 2571. The robotic mount can slide along the horizontal span 2550 and is also able to couple to a coupler extension 2570. In one embodiment of the disclosure, the coupler extension 2570 is an integral part of the robotic mount 2571 and is able to then attach to various robotic catheter heads 2505 that can be used in procedures. In a separate embodiment, the coupler extension 2570 is instead coupled to the robotic catheter head 2505 and the joined coupler extension 2570 and robotic catheter head 2505 can then be interchanged with various robotic mounts 2571. In the embodiment of FIG. 25, the coupler extension 2570 can move forward and backward within the robotic mount 2571. The coupler extension 2570 can also adjust the pitch and yaw of the robotic catheter head 2505. An adjustment support 2515 can also be included at a distal end of the robotic catheter head 2505 to allow for direction and kinking resistance of any medical device attached.

Figure 26:
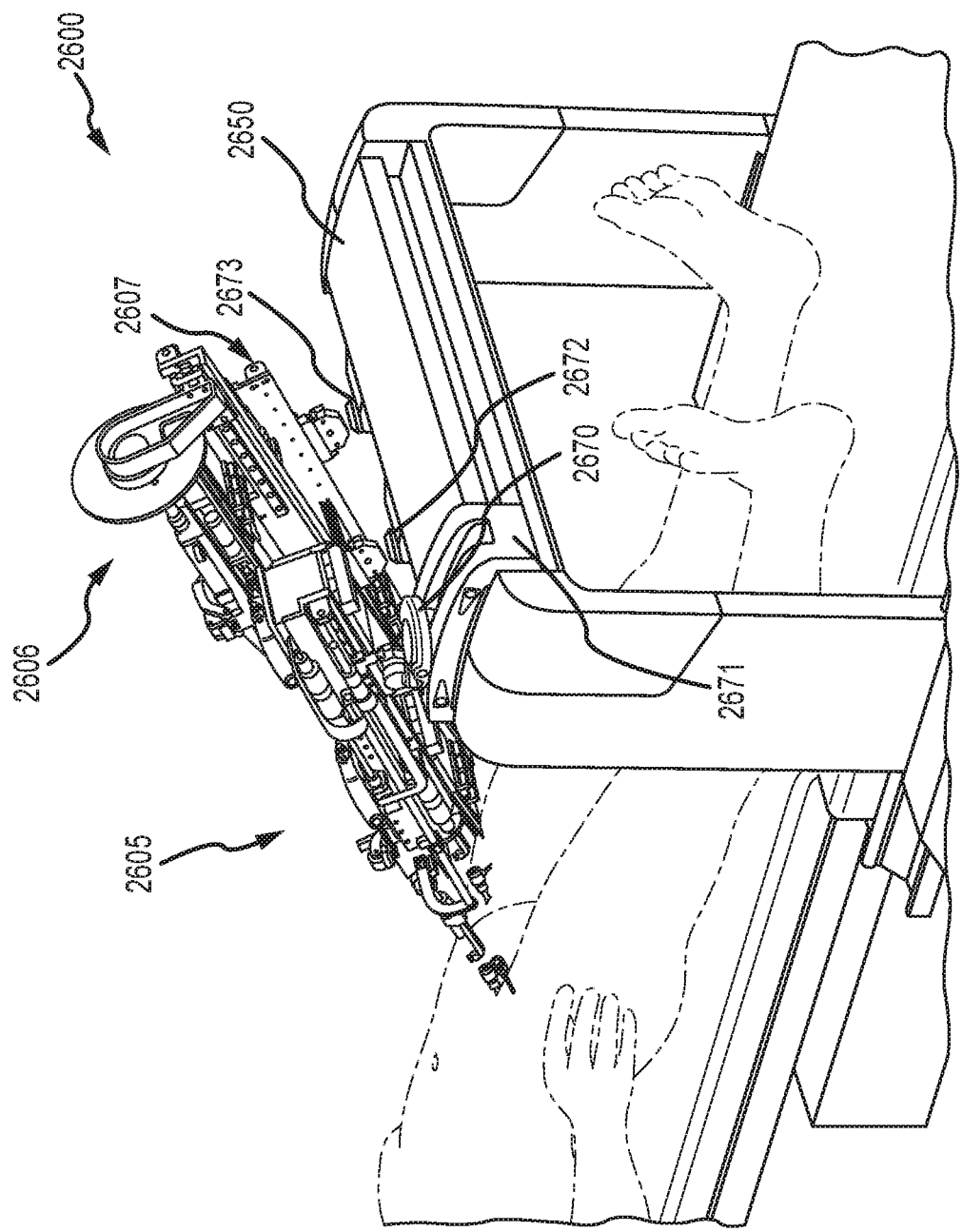
FIGS. 26-27 are enlarged isometric views of an embodiment of a robotic catheter system positioned near a patient for a procedure.
Figure 27:
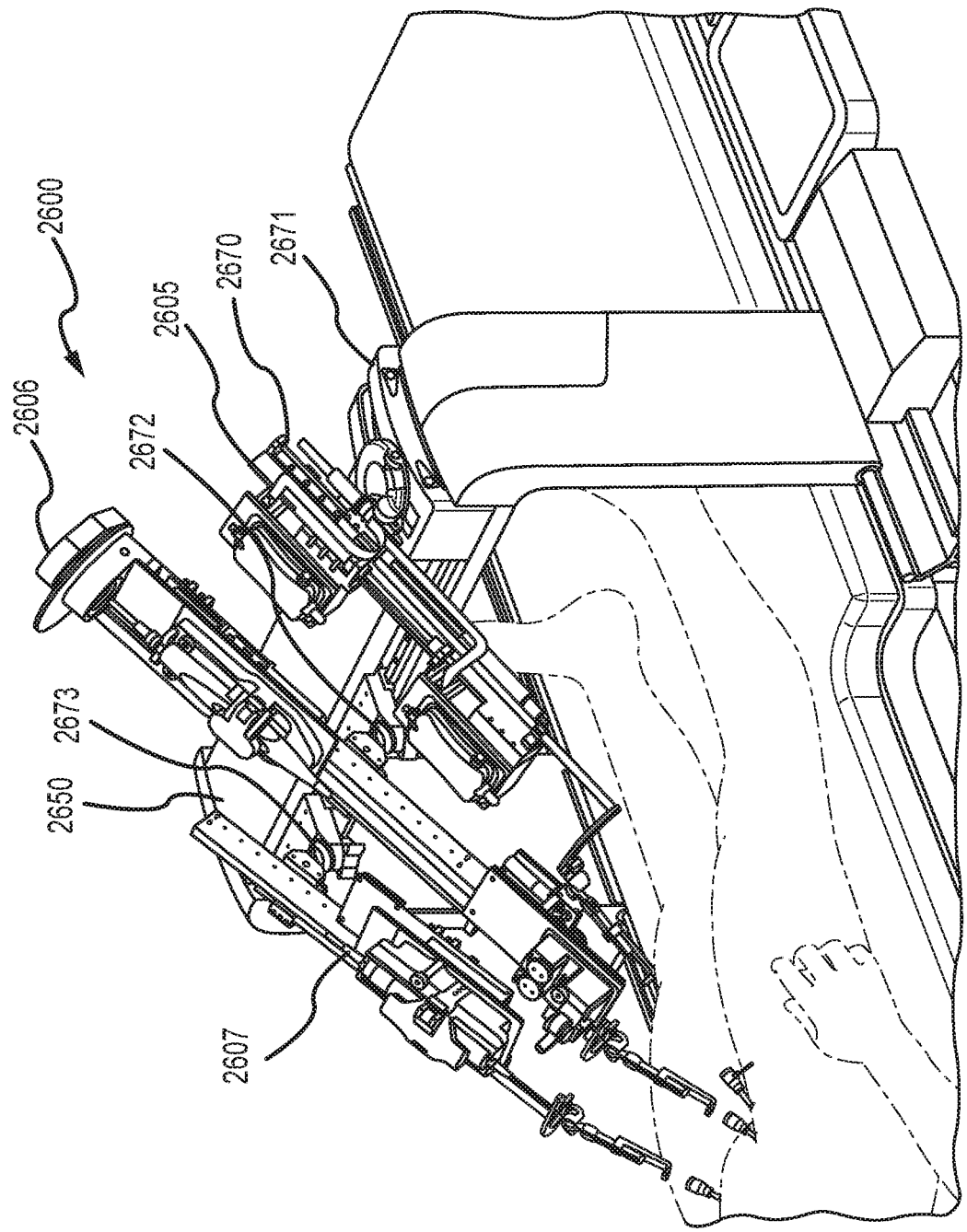

FIGS. 26-27 depict another embodiment of the disclosure. This arch-shaped suspension system 2600 is similar to that of FIG. 25 but includes a first robotic catheter head 2605, a second robotic catheter head 2606, and a third robotic catheter head 2607. The second and third robotic catheter heads are also operably coupled to the horizontal span 2650. A first coupler extension 2670 joins the first robotic catheter head 2605 to the horizontal span 2650, a second coupler extension 2672 joins the second robotic catheter head 2606 to the horizontal span 2650, and a third coupler extension 2673 joins the third robotic catheter head 2607 to the horizontal span 2650. In this embodiment the second robotic catheter head 2606 can comprise a rotatable mapping catheter or other medical device. The third robotic catheter head 2607 can comprise an ultrasound catheter or other medical device. In the embodiment of FIG. 26, the coupler extension 2670 can move forward and backward within a robotic mount 2671. The second coupler extension 2672 and third coupler extension 2673 can be of a variety that only allows adjustment of the pitch of the attached robotic catheter head or can be of a variety that allows adjustment of the pitch, yaw, extension, pan, and rotation among others. The coupler extension that is used can depend on the amount of positioning control needed for various medical devices.

Figure 28:
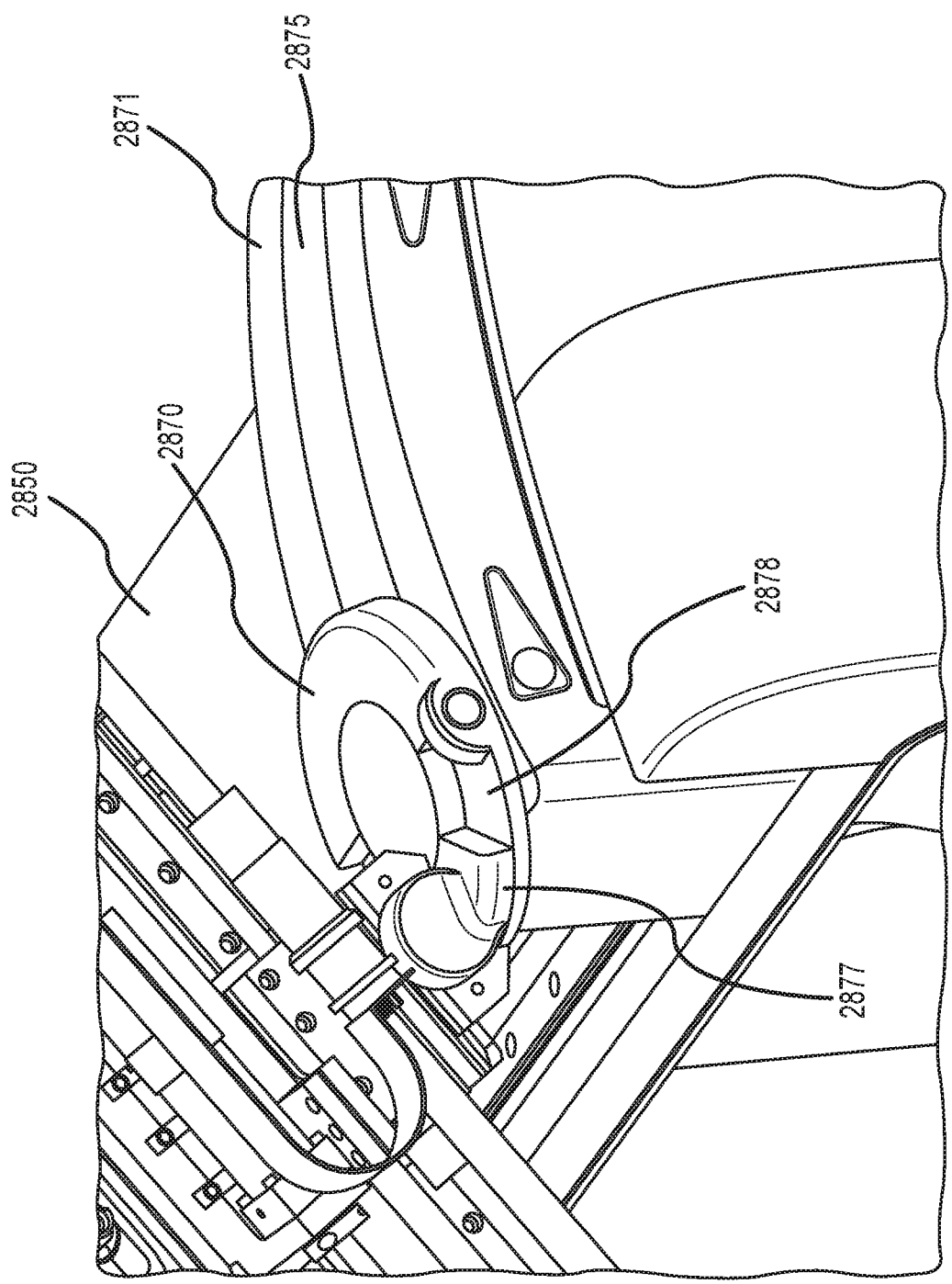
FIGS. 28-29 are enlarged isometric views of an embodiment of a robotic mount and coupler extension for use with a robotic catheter system.
Figure 29:
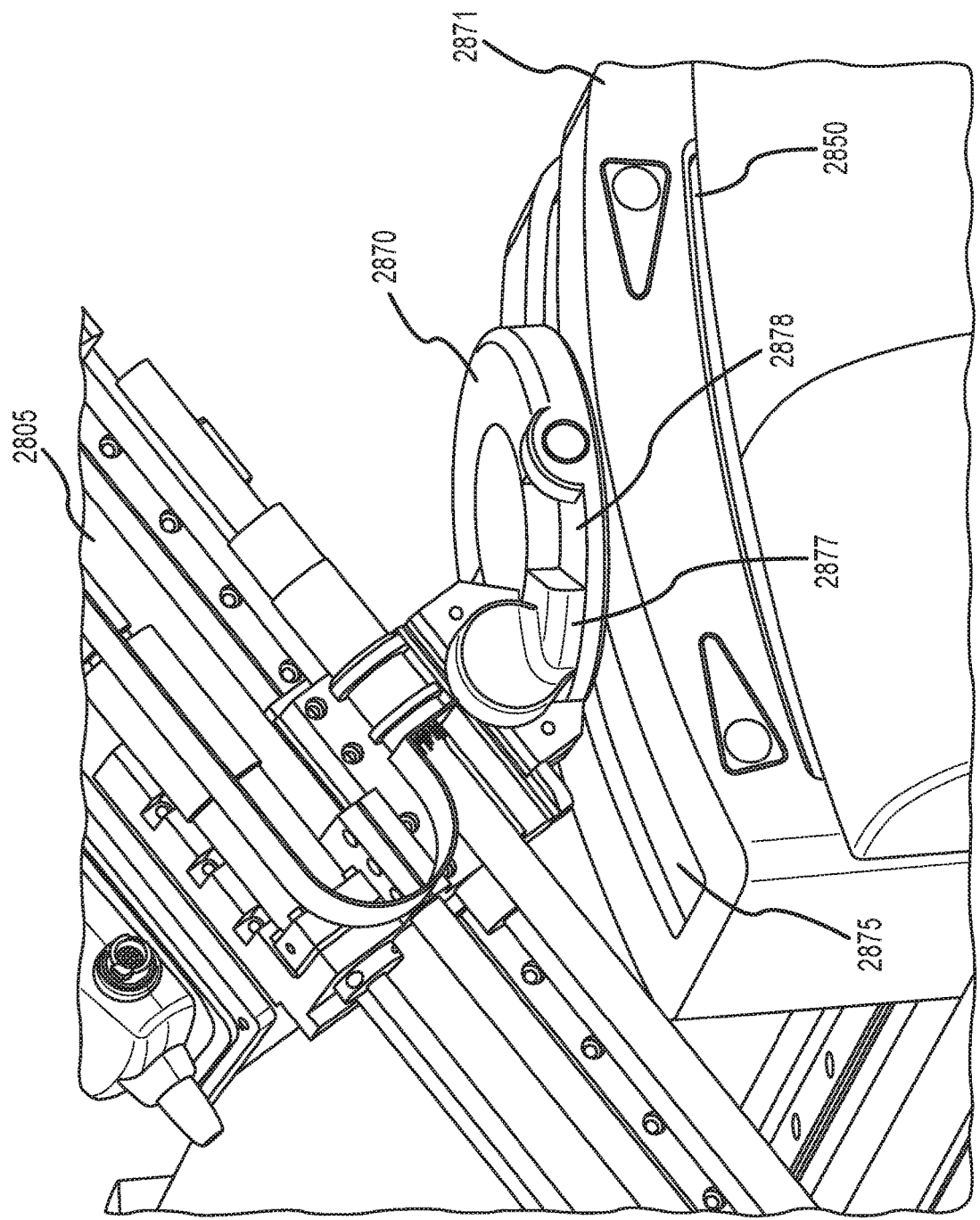

FIGS. 28-29 illustrate a close-up isometric view of a robotic catheter head 2805 attached to a coupler extension 2870 residing in an extension channel 2875 of a robotic mount 2871. The robotic mount 2871 can move along the horizontal span 2850 to allow for side to side movement of the robotic catheter head 2805. When a desired location for the robotic mount 2871 has been successfully located, an operator or user can secure the robotic mount 2871 to the horizontal span 2850 by a clamp or other securing device. In some embodiments the robotic mount contains an internal mechanism that impedes movement from a desired position. This embodiment can use mechanisms such as a resistance force, friction, or other mechanisms to resist movement In such an embodiment the user can either press a button on the equipment to lessen or remove the impediment or in some embodiments the robotic mount will move after a certain threshold force has been applied.

The extension channel 2875 allows the coupler extension 2870 to slide within the robotic mount 2871. When a desired position of the coupler extension 2870 is achieved, the robotic mount can stop the movement by clamping or otherwise retaining the coupler extension 2870 at the current location within the extension channel 2875. The yaw of the robotic catheter head 2805 can next be determined by using the rotation controller 2877 of the coupler extension 2870. The rotation controller 2877 can move within the rotation channel 2878 to allow the robotic catheter head 2805 to swivel within about 180 degrees. Other coupler extension embodiments may have rotation channels that extend farther around the coupler extension. Such an embodiment would allow for a larger range of yaw to be chosen by the user.

Although at least one embodiment of an arch-shaped suspension system for a robotic catheter system has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A robotic catheter system comprising:
   a robotic catheter head;
   an arch-shaped suspension system comprising a first vertical span, a second vertical span, and a horizontal span, wherein a first end of the horizontal span is coupled to the first vertical span and a second end of the horizontal span is coupled to the second vertical span;
   a robotic mount operably connecting the robotic catheter head to the horizontal span, wherein the robotic mount is movable along the horizontal span, wherein the robotic catheter head is configured to be slidably movable along the robotic mount in a direction different than along the horizontal span;
   a catheter clamp is operably connected to the horizontal span and to the robotic catheter head, wherein the catheter clamp is configured to allow the robotic mount to freely move along the horizontal span when in the open position and to secure the robotic mount to the horizontal span when in the closed position; and
   a suspension system cart comprising a cart body, a first cart rail and a second cart rail, and wherein the first vertical span and the second vertical span of the arch-shaped suspension system are configured to releasably couple to/from the first and second cart rails of the suspension system cart.

2. The robotic catheter system according to claim 1 wherein the suspension system cart is configured to be movable using wheels to place the first cart rail adjacent to a first extension rail of a patient bed and to place the second cart rail adjacent to a second extension rail of the patient bed.

3. The robotic catheter system according to claim 2, wherein the arch-shaped suspension system is configured to slidably move from the first and second cart rails to the first and second extension rails.

4. An arch-shaped suspension system comprising:
   a robotic catheter head, wherein the at least one robotic catheter head further comprises a catheter cartridge and a sheath cartridge;
   a first vertical span, a second vertical span, and a horizontal span, wherein the horizontal span comprises a first end and a second end, and wherein a first end of the horizontal span is coupled to the first vertical span and a second end of the horizontal span is coupled to the second vertical span, and wherein the first vertical span and the second vertical span are configured to attach to a patient bed;
   a robotic mount operably connecting the robotic catheter head to the horizontal span, wherein the robotic mount is movable along the horizontal span;
   a catheter clamp including an open position and a closed position, wherein the catheter clamp is configured to allow the robotic mount to freely move along the horizontal span when in the open position and to secure the robotic mount to the horizontal span when in the closed position; and
   a suspension system cart comprising a cart body, a first cart rail and a second cart rail, and wherein the first vertical span and the second vertical span of the arch-shaped suspension system are configured to releasably couple to/from the first and second cart rails of the suspension system cart;
   wherein the robotic catheter head is configured to be slidably movable along the robotic mount in a direction different than along the horizontal span.

5. The arch-shaped suspension system according to claim 4 further comprising a first linear guide block coupled to the first vertical span and a second linear guide block coupled to the second vertical span.

6. The arch-shaped suspension system according to claim 5, wherein the first linear guide block and the second linear guide block are configured to attach to a pair of extension members coupled to the patient bed.

7. The arch-shaped suspension system according to claim 6 wherein the pair of extension members each comprise a round linear guide rail and wherein the first and second linear guide blocks are configured to move along the pair of round linear guide rails.

8. The arch-shaped suspension system according to claim 5 wherein the first linear guide block and the second linear guide block further comprise a plurality of mounting holes for securing the first and second linear guide block to the respective first and second vertical span.

9. The robotic catheter system according to claim 3 further comprising a first and second linear guide block attached to the first and second vertical spans respectively, wherein the linear guide blocks are configured to be slidable between the patient bed and the moveable suspension system cart along the first and second extension rails of the patient bed and the first and second cart rails of the moveable suspension system cart.

* * * * *